United States Patent
Kadow et al.

(10) Patent No.: US 7,714,019 B2
(45) Date of Patent: May 11, 2010

(54) INDOLE, AZAINDOLE AND RELATED HETEROCYCLIC PYRROLIDINE DERIVATIVES

(75) Inventors: John F. Kadow, Wallingford, CT (US); Qiufen May Xue, Newbury Park, CA (US); Tao Wang, Farmington, CT (US); Zhongxing Zhang, Madison, CT (US); Nicholas A. Meanwell, East Hampton, CT (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 12/417,050

(22) Filed: Apr. 2, 2009

(65) Prior Publication Data

US 2009/0186933 A1 Jul. 23, 2009

Related U.S. Application Data

(63) Continuation of application No. 11/960,885, filed on Dec. 20, 2007, now Pat. No. 7,531,552, which is a continuation of application No. 11/511,123, filed on Aug. 28, 2006, now abandoned, which is a continuation of application No. 10/352,279, filed on Jan. 27, 2003, now abandoned.

(60) Provisional application No. 60/356,977, filed on Feb. 14, 2002.

(51) Int. Cl.
A61K 31/437 (2006.01)
C07D 471/04 (2006.01)

(52) U.S. Cl. ................................ 514/414; 548/467
(58) Field of Classification Search ............... 548/467; 514/414

See application file for complete search history.

(56) References Cited

U.S. PATENT DOCUMENTS

| | | | |
|---|---|---|---|
| 4,791,104 A | 12/1988 | Picciola et al. | |
| 5,023,265 A | 6/1991 | Scherlock et al. | |
| 5,124,327 A | 6/1992 | Greenlee et al. | |
| 5,424,329 A | 6/1995 | Boschelli et al. | |
| 5,449,787 A * | 9/1995 | Miyashita et al. | 548/362.5 |
| 6,172,085 B1 | 1/2001 | Ohkawa et al. | |

FOREIGN PATENT DOCUMENTS

| EP | 0530907 A1 | 3/1993 |
|---|---|---|
| EP | 0678508 A1 | 10/1995 |
| EP | 1069111 A1 | 1/2001 |
| WO | WO 93/01181 | 1/1993 |
| WO | WO 95/04742 | 2/1995 |
| WO | WO 96/11929 | 4/1996 |
| WO | WO 00/51984 | 9/2000 |
| WO | WO 00/76521 | 12/2000 |
| WO | WO 01/62255 | 8/2001 |
| WO | WO 02/04440 | 1/2002 |

OTHER PUBLICATIONS

Afsah, at al., "Synthesis and Reactions of N-indo1-3-ylmethylalkylamines and Related Compounds," Journal of the Chemical Society, Perkin Transactions 1: Organic and Bioorganic Chemistry (1972-1999), vol. 8, pp. 1929-1932, 1984.
Fong, et al., "Indoles and Pyridazino[4,5-b]indoles as Nonnucleoside Analog Inhibitors of HIV-1 Reverse Transcriptase," Eur. J. Med. Chem., 30, pp. 963-971, 1995.
Romero, et al., J. Med. Chem., 36, pp. 1505-1508, 1993.
Young, at al., "2-Heterocyclic Indole-3-Sulfones as Inhibitors of HIV-1 Reverse Transcriptase," Biorganic and Medicinal Chemistry Letters, 5(5), pp. 491-496, 1995.
Genin, at al., "Synthesis and Bioactivity of Novel Bis(Heteroaryl)Piperazine (BHAP) Reverse Transcriptase Inhibitors: Structure-Activity Relationships and Increased Metabolic Stability of Novel Substituted Pyridine Analogs," J. Med. Chem., 39, pp. 5267-5275, 1996.
Silvestri, et al., Antiviral Chemistry and Chemotherapy, 9, pp. 139-148, 1998.
Fredenhagen, et al., "Semicochliodinol A and B: Inhibitors of HIV-1 Protease and EGF-R Protein Tyrosine Kinase Related Asterriquinones Produced by the Fungus *Chrysosporium merdarium*," Journal of Antibiotics, 50(5), pp. 395-401, 1997.
Kato, et al., "New 5-HT$_3$ (Serotonin-3) Receptor Antagonists. IV. Synthesis and Structure-Activity Relationships of Azabicycloalkaneacetamide Derivatives," Chem. Pharm. Bull, 43(8), pp. 1351-1357, 1995.
Levacher, at al., "Broadening in the Scope of NADH Models by Using Chiral and Non-Chiral Pyrrolo [2,3-b]Pyridine Derivatives," Tetrahedron, 47(3), pp. 429-440, 1991.
Nicolau, et al., "A Novel Stragegy for the Solid-Phase Synthesis of Substituted Indolines," J. Am. Chem. Soc., 122(12), pp. 1966-1967, 2000.

* cited by examiner

*Primary Examiner*—Kamal A Saeed
*Assistant Examiner*—Janet L Coppins
(74) *Attorney, Agent, or Firm*—John F. Levis

(57) ABSTRACT

This invention provides compounds having drug and bio-affecting properties, their pharmaceutical compositions and method of use. In particular, the invention is concerned with amido piperazine derivatives. These compounds possess unique antiviral activity, whether used alone or in combination with other antivirals, antiinfectives, immunomodulators or HIV entry inhibitors. More particularly, the present invention relates to the treatment of HIV and AIDS.

2 Claims, No Drawings

INDOLE, AZAINDOLE AND RELATED HETEROCYCLIC PYRROLIDINE DERIVATIVES

REFERENCE TO RELATED APPLICATIONS

This Continuation application claims the benefit of U.S. Ser. No. 11/960,885 filed Dec. 20, 2007, now allowed, which in turn is a Continuation application which claims the benefit of U.S. Ser. No. 11/511,123 filed Aug. 28, 2006, now abandoned, which in turn is a Continuation of Ser. No. 10/352,279 filed Jan. 27, 2003, now abandoned, which claims the benefit of U.S. Provisional Application Ser. No. 60/356,977 filed Feb. 14, 2002, now expired.

FIELD OF THE INVENTION

This invention provides compounds having drug and bio-affecting properties, their pharmaceutical compositions and method of use. In particular, the invention is concerned with new heterocyclic amidopiperazine derivatives that possess unique antiviral activity. More particularly, the present invention relates to compounds useful for the treatment of HIV and AIDS.

BACKGROUND ART

HIV-1 (human immunodeficiency virus-1) infection remains a major medical problem, with an estimated 33.6 million people infected worldwide. The number of cases of HIV and AIDS (acquired immunodeficiency syndrome) has risen rapidly. In 1999, 5.6 million new infections were reported, and 2.6 million people died from AIDS. Currently available drugs for the treatment of HIV include six nucleoside reverse transcriptase (RT) inhibitors (zidovudine, didanosine, stavudine, lamivudine, zalcitabine and abacavir), three non-nucleoside reverse transcriptase inhibitors (nevirapine, delavirdine and efavirenz), and six peptidomimetic protease inhibitors (saquinavir, indinavir, ritonavir, nelfinavir, amprenavir and lopinavir). Each of these drugs can only transiently restrain viral replication if used alone. However, when used in combination, these drugs have a profound effect on viremia and disease progression. In fact, significant reductions in death rates among AIDS patients have been recently documented as a consequence of the widespread application of combination therapy. However, despite these impressive results, 30 to 50% of patients ultimately fail combination drug therapies. Insufficient drug potency, non-compliance, restricted tissue penetration and drug-specific limitations within certain cell types (e.g. most nucleoside analogs cannot be phosphorylated in resting cells) may account for the incomplete suppression of sensitive viruses. Furthermore, the high replication rate and rapid turnover of HIV-1 combined with the frequent incorporation of mutations, leads to the appearance of drug-resistant variants and treatment failures when sub-optimal drug concentrations are present (Larder and Kemp; Gulick; Kuritzkes; Morris-Jones et al; Schinazi et al; Vacca and Condra; Flexner; Berkhout and Ren et al; (Ref. 6-14)). Therefore, novel anti-HIV agents exhibiting distinct resistance patterns, and favorable pharmacokinetic as well as safety profiles are needed to provide more treatment options.

Currently marketed HIV-1 drugs are dominated by either nucleoside reverse transcriptase inhibitors or peptidomimetic protease inhibitors. Non-nucleoside reverse transcriptase inhibitors (NNRTIs) have recently gained an increasingly important role in the therapy of HIV infections (Pedersen & Pedersen, Ref 15). At least 30 different classes of NNRTI have been described in the literature (De Clercq, Ref. 16) and several NNRTIs have been evaluated in clinical trials. Dipyridodiazepinone (nevirapine), benzoxazinone (efavirenz) and bis(heteroaryl) piperazine derivatives (delavirdine) have been approved for clinical use. However, the major drawback to the development and application of NNRTIs is the propensity for rapid emergence of drug resistant strains, both in tissue cell culture and in treated individuals, particularly those subject to monotherapy. As a consequence, there is considerable interest in the identification of NNRTIs less prone to the development of resistance (Pedersen & Pedersen, Ref 15). A recent overview of non-nucleoside reverse transcriptase inhibitors: perspectives on novel therapeutic compounds and strategies for the treatment of HIV infection. has appeared (Buckheit, reference 99). A review covering both NRTI and NNRTIs has appeared (De clercq, reference 100). An overview of the current state of the HIV drugs has been published (De clercq, reference 101)

Several indole derivatives including indole-3-sulfones, piperazino indoles, pyrazino indoles, and 5H-indolo[3,2-b][1,5]benzothiazepine derivatives have been reported as HIV-1 reverse transcriptase inhibitors (Greenlee et al, Ref. 1; Williams et al, Ref. 2; Romero et al, Ref. 3; Font et al, Ref. 17; Romero et al, Ref. 18; Young et al, Ref. 19; Genin et al, Ref. 20; Silvestri et al, Ref. 21). Indole 2-carboxamides have also been described as inhibitors of cell adhesion and HIV infection (Boschelli et al, U.S. Pat. No. 5,424,329, Ref. 4). 3-substituted indole natural products (Semicochliodinol A and B, didemethylasterriquinone and isocochliodinol) were disclosed as inhibitors of HIV-1 protease (Fredenhagen et al, Ref. 22).

Structurally related aza-indole amide derivatives have been disclosed previously (Kato et al, Ref. 23; Levacher et al, Ref. 24; Dompe Spa, WO-09504742, Ref. 5(a); SmithKline Beecham PLC, WO-09611929, Ref. 5(b); Schering Corp., U.S. Pat. No. 5,023,265, Ref. 5(c)). However, these structures differ from those claimed herein in that they are aza-indole mono-amide rather than unsymmetrical aza-indole piperazine diamide derivatives, and there is no mention of the use of these compounds for treating viral infections, particularly HIV. Indole and azaindole piperazine containing derivatives have been disclosed in three different PCT patent applications (Reference 93-95) None of these applications discloses pyrrolidine compounds such as described in this invention.

Nothing in these references can be construed to disclose or suggest the novel compounds of this invention and their use to inhibit HIV infection.

REFERENCES CITED

Patent Documents

1. Greenlee, W. J.; Srinivasan, P. C. Indole reverse transcriptase inhibitors. U.S. Pat. No. 5,124,327.
2. Williams, T. M.; Ciccarone, T. M.; Saari, W. S.; Wai, J. S.; Greenlee, W. J.; Balani, S. K.; Goldman, M. E.; Theohrides, A. D. Indoles as inhibitors of HIV reverse transcriptase. European Patent 530907.
3. Romero, D. L.; Thomas, R. C.; Preparation of substituted indoles as anti-AIDS pharmaceuticals. PCT WO 93/01181.
4. Boschelli, D. H.; Connor, D. T.; Unangst, P. C. Indole-2-carboxamides as inhibitors of cell adhesion. U.S. Pat. No. 5,424,329.
5. (a) Mantovanini, M.; Melillo, G.; Daffonchio, L. Tropyl 7-azaindol-3-ylcarboxyamides as antitussive agents. PCT WO 95/04742 (Dompe Spa). (b) Cassidy, F.; Hughes, I.; Rahman, S.; Hunter, D. J. Bisheteroaryl-carbonyl and carboxamide derivatives with 5HT 2C/2B antagonists activity. PCT WO 96/11929. (c) Scherlock, M. H.; Tom, W. C. Substituted 1H-pyrrolopyridine-3-carboxamides. U.S. Pat. No. 5,023,265.

Other Publications

6. Larder, B. A.; Kemp, S. D. Multiple mutations in the HIV-1 reverse transcriptase confer high-level resistance to zidovudine (AZT). *Science,* 1989, 246, 1155-1158.
7. Gulick, R. M. Current antiretroviral therapy: An overview. *Quality of Life Research,* 1997, 6, 471-474.
8. Kuritzkes, D. R. HIV resistance to current therapies. *Antiviral Therapy,* 1997, 2 (Supplement 3), 61-67.
9. Morris-Jones, S.; Moyle, G.; Easterbrook, P. J. Antiretroviral therapies in HIV-1 infection. *Expert Opinion on Investigational Drugs,* 1997, 6(8),1049-1061.
10. Schinazi, R. F.; Larder, B. A.; Mellors, J. W. Mutations in retroviral genes associated with drug resistance. *International Antiviral News,* 1997, 5, 129-142.
11. Vacca, J. P.; Condra, J. H. Clinically effective HIV-1 protease inhibitors. *Drug Discovery Today,* 1997, 2, 261-272.
12. Flexner, D. HIV-protease inhibitors. *Drug Therapy,* 1998, 338, 1281-1292.
13. Berkhout, B. HIV-1 evolution under pressure of protease inhibitors: Climbing the stairs of viral fitness. *J. Biomed. Sci.,* 1999, 6, 298-305.
14. Ren, S.; Lien, E. J. Development of HIV protease inhibitors: A survey. *Prog. Drug Res.,* 1998, 51, 1-31.
15. Pedersen, O. S.; Pedersen, E. B. Non-nucleoside reverse transcriptase inhibitors: the NNRTI boom. *Antiviral Chem. Chemother.* 1999, 10, 285-314.
16. (a) De Clercq, E. The role of non-nucleoside reverse transcriptase inhibitors (NNRTIs) in the therapy of HIV-1 infection. *Antiviral Research,* 1998, 38, 153-179. (b) De Clercq, E. Perspectives of non-nucleoside reverse transcriptase inhibitors (NNRTIs) in the therapy of HIV infection. IL. *Farmaco,* 1999, 54, 26-45.
17. Font, M.; Monge, A.; Cuartero, A.; Elorriaga, A.; Martinez-Irujo, J. J.; Alberdi, E.; Santiago, E.; Prieto, I.; Lasarte, J. J.; Sarobe, P. and Borras, F. Indoles and pyrazino [4,5-b]indoles as nonnucleoside analog inhibitors of HIV-1 reverse transcriptase. *Eur. J. Med. Chem.,* 1995, 30, 963-971.
18. Romero, D. L.; Morge, R. A.; Genin, M. J.; Biles, C.; Busso, M.; Resnick, L.; Althaus, I. W.; Reusser, F.; Thomas, R. C and Tarpley, W. G. Bis(heteroaryl)piperazine (BHAP) reverse transcriptase inhibitors: structure-activity relationships of novel substituted indole analogues and the identification of 1-[(5-methanesulfonamido-1H-indol-2-yl)-carbonyl]-4-[3-[1-methylethyl)amino]-pyridinyl]piperazine momomethansulfonate (U-90152S), a second generation clinical candidate. *J. Med. Chem.,* 1993, 36, 1505-1508.
19. Young, S. D.; Amblard, M. C.; Britcher, S. F.; Grey, V. E.; Tran, L. O.; Lumma, W. C.; Huff, J. R.; Schleif, W. A.; Emini, E. E.; O'Brien, J. A.; Pettibone, D. J. 2-Heterocyclic indole-3-sulfones as inhibitors of HIV-reverse transcriptase. *Bioorg. Med. Chem. Lett.,* 1995, 5, 491-496.
20. Genin, M. J.; Poel, T. J.; Yagi, Y.; Biles, C.; Althaus, I.; Keiser, B. J.; Kopta, L. A.; Friis, J. M.; Reusser, F.; Adams, W. J.; Olmsted, R. A.; Voorman, R. L.; Thomas, R. C. and Romero, D. L. Synthesis and bioactivity of novel bis(heteroaryl)piperazine (BHAP) reverse transcriptase inhibitors: structure-activity relationships and increased metabolic stability of novel substituted pyridine analogs. *J. Med. Chem.,* 1996, 39, 5267-5275.
21. Silvestri, R.; Artico, M.; Bruno, B.; Massa, S.; Novellino, E.; Greco, G.; Marongiu, M. E.; Pani, A.; De Montis, A and La Colla, P. Synthesis and biological evaluation of 5H-indolo[3,2-b][1,5]benzothiazepine derivatives, designed as conformationally constrained analogues of the human immunodeficiency virus type 1 reverse transcriptase inhibitor L-737,126. *Antiviral Chem. Chemother.* 1998, 9, 139-148.
22. Fredenhagen, A.; Petersen, F.; Tintelnot-Blomley, M.; Rosel, J.; Mett, H and Hug, P. J. Semicochliodinol A and B: Inhibitors of HIV-1 protease and EGF-R protein Tyrosine Kinase related to Asterriquinones produced by the fungus *Chrysosporium nerdarium. Antibiotics,* 1997, 50, 395-401.
23. Kato, M.; Ito, K.; Nishino, S.; Yamakuni, H.; Takasugi, H. New 5-HT$_3$ (Serotonin-3) receptor antagonists. IV. Synthesis and structure-activity relationships of azabicycloalkaneacetamide derivatives. *Chem. Pharm. Bull.,* 1995, 43, 1351-1357.
24. Levacher, V.; Benoit, R.; Duflos, J; Dupas, G.; Bourguignon, J.; Queguiner, G. Broadening the scope of NADH models by using chiral and non chiral pyrrolo[2,3-b]pyridine derivatives. *Tetrahedron,* 1991, 47, 429-440.
25. Shadrina, L. P.; Dormidontov, Yu. P.; Ponomarev, V. G.; Lapkin, I. I. Reactions of organomagnesium derivatives of 7-aza- and benzoindoles with diethyl oxalate and the reactivity of ethoxalylindoles. *Khim. Geterotsikl. Soedin.,* 1987, 1206-1209.
26. Sycheva, T. V.; Rubtsov, N. M.; Sheinker, Yu. N.; Yakhontov, L. N. Some reactions of 5-cyano-6-chloro-7-azaindoles and lactam-lactim tautomerism in 5-cyano-6-hydroxy-7-azaindolines. *Khim. Geterotsikl. Soedin.,* 1987, 100-106.
27. (a) Desai, M.; Watthey, J. W. H.; Zuckerman, M. A convenient preparation of 1-aroylpiperazines. *Org. Prep. Proced. Int.,* 1976, 8, 85-86. (b) Adamczyk, M.; Fino, J. R. Synthesis of procainamide metabolites. N-acetyl desethylprocainamide and desethylprocainamide. *Org. Prep. Proced. Int.* 1996, 28, 470-474. (c) Rossen, K.; Weissman, S. A.; Sager, J.; Reamer, R. A.; Askin, D.; Volante, R. P.; Reider, P. J. Asymmetric Hydrogenation of tetrahydropyrazines: Synthesis of (S)-piperazine 2-tert-butylcarboxamide, an intermediate in the preparation of the HIV protease inhibitor Indinavir. *Tetrahedron Lett.,* 1995, 36, 6419-6422. (d) Wang, T.; Zhang, Z.; Meanwell, N. A. Benzoylation of Dianions: Preparation of mono-Benzoylated Symmetric Secondary Diamines. *J. Org. Chem.,* 1999, 64, 7661-7662.
28. Li, H.; Jiang, X.; Ye, Y.-H.; Fan, C.; Romoff, T.; Goodman, M. 3-(Diethoxyphosphoryloxy)-1,2,3-benzotriazin-4 (3H)-one (DEPBT): A new coupling reagent with remarkable resistance to racemization. *Organic Lett.,* 1999, 1, 91-93.
29. Harada, N.; Kawaguchi, T.; Inoue, I.; Ohashi, M.; Oda, K.; Hashiyama, T.; Tsujihara, K. Synthesis and antitumor activity of quaternary salts of 2-(2'-oxoalkoxy)-9-hydroxyellipticines. *Chem. Pharm. Bull.,* 1997, 45, 134-137.
30. Schneller, S. W.; Luo, J.-K. Synthesis of 4-amino-1H-pyrrolo[2,3-b]pyridine (1,7-Dideazaadenine) and 1H-pyrrolo[2,3-b]pyridin-4-ol (1,7-Dideazahypoxanthine). *J. Org. Chem.,* 1980, 45, 4045-4048.
31. Shiotani, S.; Tanigochi, K. Furopyridines. XXII [1]. Elaboration of the C-substitutents alpha to the heteronitrogen atom of furo[2,3-b]-, -[3,2-b]-, -[2,3-c]- and -[3,2-c] pyridine. *J. Het. Chem.,* 1997, 34, 901-907.

32. Minakata, S.; Komatsu, M.; Ohshiro, Y. Regioselective functionalization of 1H-pyrrolo[2,3-b]pyridine via its N-oxide. *Synthesis,* 1992, 661-663.
33. Klemm, L. H.; Hartling, R. Chemistry of thienopyridines. XXIV. Two transformations of thieno[2,3-b]pyridine 7-oxide (1). *J. Het. Chem.,* 1976, 13, 1197-1200.
34. Antonini, I.; Claudi, F.; Cristalli, G.; Franchetti, P.; Crifantini, M.; Martelli, S. Synthesis of 4-amino-1-D-ribofuranosyl-1H-pyrrolo[2,3-b]pyridine (1-Deazatubercidin) as a potential antitumor agent. *J. Med. Chem.,* 1982, 25, 1258-1261.
35. (a) Regnouf De Vains, J. B.; Papet, A. L.; Marsura, A. New symmetric and unsymmetric polyfunctionalized 2,2'-bipyridines. *J. Het. Chem.,* 1994, 31, 1069-1077. (b) Miura, Y.; Yoshida, M.; Hamana, M. Synthesis of 2,3-fused quinolines from 3-substituted quinoline 1-oxides. Part II, *Heterocycles,* 1993, 36, 1005-1016. (c) Profft, V. E.; Rolle, W. Uber 4-merkaptoverbindungendes 2-methylpyridins. *J. Prakt. Chem.,* 1960, 283 (11), 22-34.
36. Nesi, R.; Giomi, D.; Turchi, S.; Tedeschi, P., Ponticelli, F. A new one step synthetic approach to the isoxazolo[4,5-b] pyridine system. *Synth. Comm.,* 1992, 22, 2349-2355.
37. (a) Walser, A.; Zenchoff, G.; Fryer, R. I. Quinazolines and 1,4-benzodiazepines. 75. 7-Hydroxyaminobenzodiazepines and derivatives. *J. Med. Chem.,* 1976, 19, 1378-1381. (b) Barker, G.; Ellis, G. P. Benzopyrone. Part I. 6-Amino- and 6-hydroxy-2-substituted chromones. *J. Chem. Soc.,* 1970, 2230-2233.
38. Ayyangar, N. R.; Lahoti, R J.; Daniel, T. An alternate synthesis of 3,4-diaminobenzophenone and mebendazole. *Org. Prep. Proced. Int.,* 1991, 23, 627-631.
39. Mahadevan, I.; Rasmussen, M. Ambident heterocyclic reactivity: The alkylation of pyrrolopyridines (azaindoles, diazaindenes). *Tetrahedron,* 1993, 49, 7337-7352.
40. Chen, B. K.; Saksela, K.; Andino, R.; Baltimore, D. Distinct modes of human immunodeficiency type 1 proviral latency revealed by superinfection of nonproductively infected cell lines with recombinant luciferase-encoding viruses. *J. Virol.,* 1994, 68, 654-660.
41. Bodanszky, M.; Bodanszky, A. "*The Practice of Peptide Synthesis*"$2^{nd}$ Ed., Springer-Verlag: Berlin Heidelberg, Germany, 1994.
42. Albericio, F. et al. *J. Org. Chem.* 1998, 63, 9678.
43. Knorr, R. et al. *Tetrahedron Lett.* 1989, 30, 1927.
44. (a) Jaszay Z. M. et al. *Synth. Commun.,* 1998 28, 2761 and references cited therein; (b) Bernasconi, S. et al. *Synthesis,* 1980, 385.
45. (a) Jaszay Z. M. et al. *Synthesis,* 1989, 745 and references cited therein; (b) Nicolaou, K. C. et al. *Angew. Chem. Int. Ed.* 1999, 38, 1669.
46. Ooi, T. et al. *Synlett.* 1999, 729.
47. Ford, R. E. et al. *J. Med. Chem.* 1986, 29, 538.
48. (a) Yeung, K.-S. et al. Bristol-Myers Squibb Unpublished Results. (b) Wang, W. et al. *Tetrahedron Lett.* 1999, 40, 2501.
49. Brook, M. A. et al. *Synthesis,* 1983, 201.
50. Yamazaki, N. et al. *Tetrahedron Lett.* 1972, 5047.
51. Barry A. Bunin "The Combinatorial Index" 1998 Academic Press, San Diego/London pages 78-82.
52. Richard C. Larock Comprehensive Organic Transormations 2nd Ed. 1999, John Wiley and Sons New York.
53. M. D. Mullican et. al. *J. Med. Chem.* 1991, 34, 2186-2194.
54. Protective groups in organic synthesis 3rd ed./Theodora W. Greene and Peter G. M. Wuts. New York: Wiley, 1999.
55. Katritzky, Alan R. Lagowski, Jeanne M. The principles of heterocyclic Chemistry New York: Academic Press, 1968
56. Paquette, Leo A. Principles of modern heterocyclic chemistry New York: Benjamin.
57. Katritzky, Alan R.; Rees, Charles W.; Comprehensive heterocyclic chemistry: the structure, reactions, synthesis, and uses of heterocyclic compounds 1st ed. Oxford (Oxfordshire); New York: Pergamon Press, 1984. 8 v.
58. Katritzky, Alan R Handbook of heterocyclic 1st ed Oxford (Oxfordshire) New York: Pergamon Press, 1985.
59. Davies, David I Aromatic Heterocyclic Oxford; New York: Oxford University Press, 1991.
60. Ellis, G. P. Synthesis of fused Chichester [Sussex]; New York: Wiley, c1987-c1992. Chemistry of heterocyclic compounds; v. 47.
61. Joule, J. A Mills, K., Smith, G. F. Heterocyclic Chemistry, 3rd ed London; New York Chapman & Hall, 1995.
62. Katritzky, Alan R., Rees, Charles W., Scriven, Eric F. V. Comprehensive heterocyclic chemistry II: a review of the literature 1982-1995.
63. The structure, reactions, synthesis, and uses of heterocyclic compounds 1st ed. Oxford; New York: Pergamon, 1996. 11 v. in 12: ill.; 28 cm.
64. Eicher, Theophil, Hauptmann, Siegfried. The chemistry of heterocycles structure, reactions, syntheses, and applications Stuttgart; New York: G. Thieme, 1995.
65. Grimmett, M. R. Imidazole and benzimidazole Synthesis London; San Diego: Academic Press, 1997.
66. Advances in heterocyclic chemistry. Published in New York by Academic Press, starting in 1963-present.
67. Gilchrist, T. L. (Thomas Lonsdale) Heterocyclic chemistry 3rd ed. Harlow, Essex: Longman, 1997. 414 p.: ill.; 24 cm.
68. Farina, Vittorio; Roth, Gregory P. Recent advances in the Stille reaction; *Adv. Met.-Org. Chem.* 1996, 5, 1-53.
69. Farina, Vittorio; Krishnamurthy, Venkat; Scott, William J. The Stille reaction; Org. React. (N.Y.) (1997), 50, 1-652.
70. Stille, J. K. *Angew. Chem. Int. Ed. Engl.* 1986, 25, 508-524.
71. Norio Miyaura and Akiro Suzuki *Chem. Rev.* 1995, 95, 2457.
72. Home, D. A. *Heterocycles* 1994, 39, 139.
73. Kamitori, Y. et. al. *Heterocycles,* 1994, 37(1), 153.
74. Shawali, J. *Heterocyclic Chem.* 1976, 13, 989.
75. a) Kende, A. S. et al. *Org. Photochem. Synth.* 1972, 1, 92. b) Hankes, L. V.; *Biochem. Prep.* 1966, 11, 63. c) *Synth. Meth.* 22, 837.
76. Hulton et. al. *Synth. Comm.* 1979, 9, 789.
77. Pattanayak, B. K. et. al. *Indian J. Chem.* 1978, 16, 1030.
78. *Chemische Berichte* 1902, 35, 1545.
79. *Chemische Berichte* Ibid 1911, 44, 493.
80. Moubarak, I., Vessiere, R. *Synthesis* 1980, Vol. 1, 52-53.
81. *Ind J. Chem.* 1973, 11, 1260.
82. Roomi et. al. *Can J. Chem.* 1970, 48, 1689.
83. Sorrel, T. N. *J. Org. Chem.* 1994, 59, 1589.
84. Nitz, T. J. et. al. *J. Org. Chem.* 1994, 59, 5828-5832.
85. Bowden, K. et. al. *J. Chem. Soc.* 1946, 953.
86. Nitz, T. J. et. al. *J. Org. Chem.* 1994, 59, 5828-5832.
87. Scholkopf et. al. *Angew. Int. Ed. Engl.* 1971, 10(5), 333.
88. (a) Behun, J. D.; Levine, R. *J. Org. Chem.* 1961, 26, 3379. (b) Rossen, K.; Weissman, S. A.; Sager, J.; Reamer, R. A.; Askin, D.; Volante, R. P.; Reider, P. J. Asymmetric Hydrogenation of tetrahydropyrazines: Synthesis of (S)-piperazine 2-tert-butylcarboxamide, an intermediate in the preparation of the HIV protease inhibitor Indinavir. *Tetrahedron Lett.,* 1995, 36, 6419-6422. (c) Jenneskens, L. W.; Mahy, J.; den Berg, E. M. M. de B.-v.; Van der Hoef, I.; Lugtenburg, J. *Recl. Trav. Chim. Pays-Bas* 1995, 114, 97.

7

89. Wang, T.; Zhang, Z.; Meanwell, N. A. Benzoylation of Dianions: Preparation of mono-Benzoylated Symmetric Secondary Diamines. *J. Org. Chem.*, 1999, 64, 7661-7662.
90. (a) Adamczyk, M.; Fino, J. R. Synthesis of procainamide metabolites. N-acetyl desethylprocainamide and desethylprocainamide. *Org. Prep. Proced. Int.* 1996, 28, 470-474. (b) Wang, T.; Zhang, Z.; Meanwell, N. A. Regioselective mono-Benzoylation of Unsymmetrical piperazines. *J. Org. Chem.*, in press.
91. Masuzawa, K.; Kitagawa, M.; Uchida, H. *Bull Chem. Soc. Jpn.* 1967, 40, 244-245.
92. Furber, M.; Cooper, M. E.; Donald, D. K. *Tetrahedron Lett.* 1993, 34, 1351-1354.
93. Blair, Wade S.; Deshpande, Milind; Fang, Haiquan; Lin, Pin-fang; Spicer, Timothy P.; Wallace, Owen B.; Wang, Hui; Wang, Tao; Zhang, Zhongxing; Yeung, Kap-sun. Preparation of antiviral indoleoxoacetyl piperazine derivatives. PCT Int. Appl. (2000), 165 pp. WO 0076521 A1
94. Wang, Tao; Wallace, Owen B.; Zhang, Zhongxing; Meanwell, Nicholas A.; Bender, John A. Preparation of antiviral azaindole derivatives. PCT Int. Appl. (2001), WO 0162255 A1
95. Wallace, Owen B.; Wang, Tao; Yeung, Kap-Sun; Pearce, Bradley C.; Meanwell, Nicholas A.; Qiu, Zhilei; Fang, Haiquan; Xue, Qiufen May; Yin, Zhiwei. Composition and antiviral activity of substituted indoleoxoacetic piperazine derivatives. PCT Int. Appl. (2002), WO 0204440 A1
96. J. L. Marco, S. T. Ingate, and P. M. Chinchon Tetrahedron 1999, 55, 7625-7644.
97. C. Thomas, F. Orecher, and P. Gmeiner Synthesis 1998, 1491.
98. M. P. Pavia, S. J. Lobbestael, C. P. Taylor, F. M. Hershenson, and D. W. Miskell
99. Buckheit, Robert W., Jr. Expert Opinion on Investigational Drugs 2001, 10(8), 1423-1442.
100. Balzarini, J.; De Clercq, E. Antiretroviral Therapy 2001, 31-62.
101. E. De clercq Journal of Clinical Virology, 2001, 22, 73-89.
102. Merour, Jean-Yves; Joseph, Benoit. Curr. Org. Chem. (2001), 5(5), 471-506.

SUMMARY OF THE INVENTION

The present invention comprises compounds of Formula I, their pharmaceutical formulations, and their use in patients suffering from or susceptible to a virus such as HIV. The compounds of Formula I, which include nontoxic pharmaceutically acceptable salts and/or hydrates thereof, have the formula and meaning as described below. Each embodiment of a particular aspect of the invention depends from the preceding embodiment unless otherwise stated.

SUMMARY DESCRIPTION OF THE INVENTION

The present invention comprises compounds of Formula I, or pharmaceutically acceptable salts thereof, which are effective antiviral agents, particularly as inhibitors of HIV.

A first embodiment of a first aspect of the invention are compounds of Formula I, including pharmaceutically acceptable salts thereof,

8

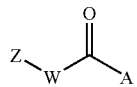

wherein:

Z is

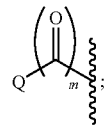

Q is selected from the group consisting of:

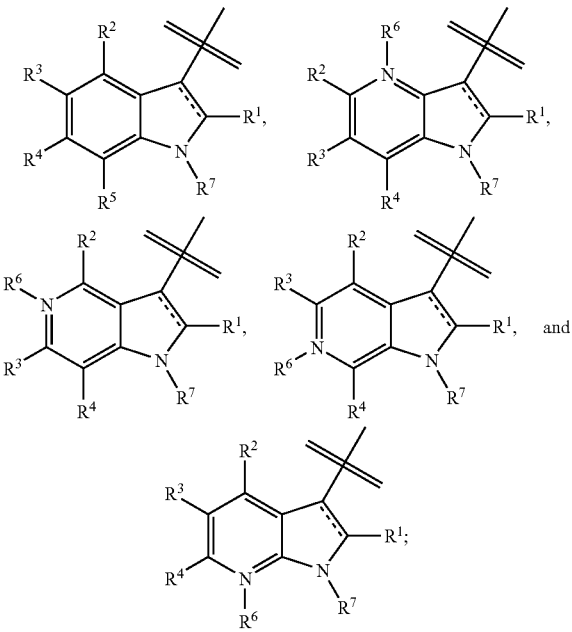

$R^1$, $R^2$, $R^3$, $R^4$ and $R^5$, are independently selected from the group consisting of hydrogen, halogen, cyano, nitro, $COOR^8$, $XR^{57}$, and B;

m is 1 or 2;

$R^7$ is $(CH_2)_n R^{44}$ wherein n is 0-6;

$R^6$ is O or does not exist;

- - represents a carbon-carbon bond or does not exist;

A is selected from the group consisting of $C_{1-6}$alkoxy, phenyl and D; wherein D is selected from the group consisting of pyridinyl, pyrimidinyl, pyrazinyl, triazinyl, furanyl, thienyl, pyrrolyl, imidazolyl, thiazolyl, isothiazolyl, oxazolyl, isoxazolyl, quinolinyl, isoquinolinyl, benzofuranyl, benzothienyl, benzoimidazolyl and benzothiazolyl; wherein said phenyl and D are independently optionally substituted with one or two of the same or different amino, halogen or trifluoromethyl;

—W— is

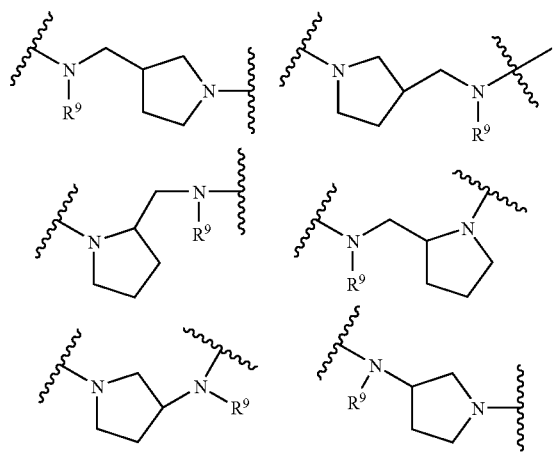

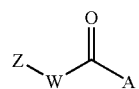

wherein:

Z is

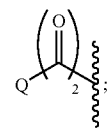

A is selected from the group consisting of phenyl and D; wherein D is selected from the group consisting of pyridinyl, furanyl and thienyl; wherein phenyl and D are independently optionally substituted with one or two of the same or different amino or halogen;

W is selected from the group consisting of

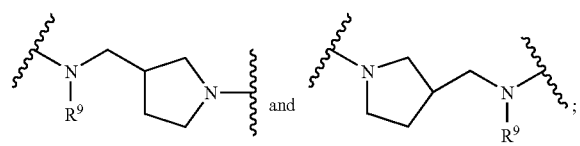

$R^1$ is hydrogen; and

Q is a member selected from groups (A) and (B) consisting of

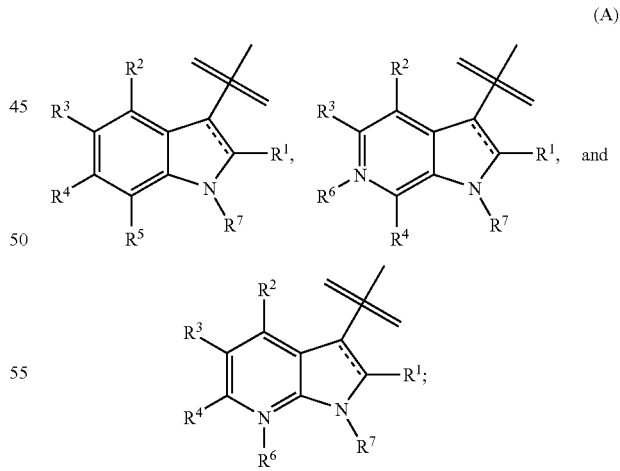

provided $R^2$ and $R^3$ are each independently hydrogen, methoxy or halogen; and $R^4$ and $R^5$ are selected from the group consisting of hydrogen, halogen, cyano, $COOR^8$, $C(O)NHCH_3$, $C(O)NH$heteroaryl, and heteroaryl; and B is selected from the group consisting of $(C_{1-6})$alkyl, $(C_{3-6})$ cycloalkyl, $C(O)NR^{40}R^{41}$, phenyl and heteroaryl; wherein said $(C_{1-6})$alkyl, phenyl and heteroaryl are independently optionally substituted with one to three same or different halogens or from one to three same or different substituents selected from F;

F is selected from the group consisting of $(C_{1-6})$alkyl, phenyl, hydroxy, $(C_{1-6})$alkoxy, halogen, benzyl, $—NR^{42}C(O)—(C_{1-6})$alkyl, $—NR^{42}R^{43}$, $COOR^{54}$ and $—CONR^{42}$; wherein said $(C_{1-6})$alkyl is optionally substituted with one to three same or different halogen;

$R^8$ is selected from the group consisting of hydrogen and $(C_{1-6})$alkyl;

$R^9$ is selected from the group consisting of hydrogen and methyl;

X is selected from the group consisting of $NR^9$, O and S;

$R^{40}$ and $R^{41}$ are independently selected from the group consisting of hydrogen, $(C_{1-6})$alkyl, $(C_{1-6})$alkoxy, phenyl and heteroaryl; wherein said phenyl and heteroaryl are independently optionally substituted with one to three same or different halogen, methyl, or $CF_3$ groups;

$R^{42}$ and $R^{43}$ are independently selected from the group consisting of hydrogen and $(C_{1-6})$alkyl;

$R^{44}$ is selected from the group consisting of H, $(C_{1-6})$alkyl, $CO(C_{1-6})$alkyl, $C(O)$-phenyl and $—CONR_aR_b$;

$R_a$ and $R_b$ are each independently H, $(C_{1-6})$alkyl or phenyl;

$R^{54}$ is selected from the group consisting of hydrogen and $(C_{1-6})$alkyl;

$R^{57}$ is $(C_{1-6})$alkyl; and heteroaryl is selected from the group consisting of pyridinyl, pyrazinyl, pyridazinyl, pyrimidinyl, furanyl, thienyl, benzothienyl, thiazolyl, isothiazolyl, oxazolyl, benzooxazolyl, isoxazolyl, imidazolyl, benzoimidazolyl, 1H-imidazo[4,5-b]pyridin-2-yl, 1H-imidazo[4,5-c]pyridin-2-yl, oxadiazolyl, thiadiazolyl, pyrazolyl, tetrazolyl, tetrazinyl, triazinyl and triazolyl.

A more preferred embodiment of a first aspect of the invention are compounds of Formula I, including pharmaceutically acceptable salts thereof,

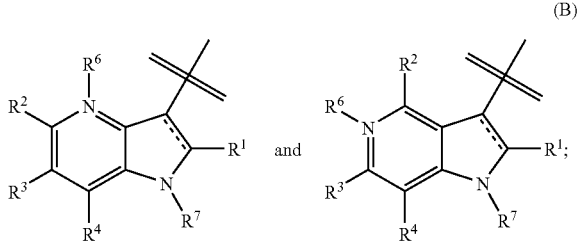

(B)

provided R² is hydrogen, methoxy or halogen;
R³ and R⁴ are selected from the group consisting of hydrogen, halogen, methoxy, cyano, COOR⁸, C(O)NHCH₃, C(O)NHheteroaryl and heteroaryl; and R⁶ does not exist;
and - - represents a carbon-carbon bond in (A) and (B).

Another embodiment of the present invention is a method for treating mammals infected with a virus, wherein said virus is HIV, comprising administering to said mammal an antiviral effective amount of a compound of Formula I, and one or more pharmaceutically acceptable carriers, excipients or diluents; optionally the compound of Formula I can be administered in combination with an antiviral effective amount of an AIDS treatment agent selected from the group consisting of: (a) an AIDS antiviral agent; (b) an anti-infective agent; (c) an immunomodulator; and (d) HIV entry inhibitors.

Another embodiment of the present invention is a pharmaceutical composition comprising an antiviral effective amount of a compound of Formula I and one or more pharmaceutically acceptable carriers, excipients, diluents and optionally in combination with an antiviral effective amount of an AIDS treatment agent selected from the group consisting of: (a) an AIDS antiviral agent; (b) an anti-infective agent; (c) an immunomodulator; and (d) HIV entry inhibitors.

DETAILED DESCRIPTION OF THE INVENTION

Since the compounds of the present invention, may possess asymmetric centers and therefore occur as mixtures of diastereomers and enantiomers, the present invention includes the individual diastereoisomeric and enantiomeric forms of the compounds of Formula I in addition to the mixtures thereof.

DEFINITIONS

The term "$C_{1-6}$ alkyl" as used herein and in the claims (unless specified otherwise) mean straight or branched chain alkyl groups such as methyl, ethyl, propyl, isopropyl, butyl, isobutyl, t-butyl, amyl, hexyl and the like.

"Halogen" refers to chlorine, bromine, iodine or fluorine.

An "aryl" group refers to an all carbon monocyclic or fused-ring polycyclic (i.e., rings which share adjacent pairs of carbon atoms) groups having a completely conjugated pi-electron system. Examples, without limitation, of aryl groups are phenyl, napthalenyl and anthracenyl. The aryl group may be substituted or unsubstituted. When substituted the substituted group(s) is preferably one or more selected from alkyl, cycloalkyl, aryl, heteroaryl, heteroalicyclic, hydroxy, alkoxy, aryloxy, heteroaryloxy, heteroalicycloxy, thiohydroxy, thioaryloxy, thioheteroaryloxy, thioheteroalicycloxy, cyano, halogen, nitro, carbonyl, O-carbamyl, N-carbamyl, C-amido, N-amido, C-carboxy, O-carboxy, sulfinyl, sulfonyl, sulfonamido, trihalomethyl, ureido, amino and —NR$^x$R$^y$, wherein R$^x$ and R$^y$ are independently selected from the group consisting of hydrogen, alkyl, cycloalkyl, aryl, carbonyl, C-carboxy, sulfonyl, trihalomethyl, and, combined, a five- or six-member heteroalicyclic ring.

As used herein, a "heteroaryl" group refers to a monocyclic or fused ring (i.e., rings which share an adjacent pair of atoms) group having in the ring(s) one or more atoms selected from the group consisting of nitrogen, oxygen and sulfur and, in addition, having a completely conjugated pi-electron system. It should be noted that the term heteroaryl is intended to encompass an N-oxide of the parent heteroaryl if such an N-oxide is chemically feasible as is known in the art. Examples, without limitation, of heteroaryl groups are furyl, thienyl, benzothienyl, thiazolyl, imidazolyl, oxazolyl, oxadiazolyl, thiadiazolyl, benzothiazolyl, triazolyl, tetrazolyl, isoxazolyl, isothiazolyl, pyrrolyl, pyranyl, tetrahydropyranyl, pyrazolyl, pyridyl, pyrimidinyl, quinolinyl, isoquinolinyl, purinyl, carbazolyl, benzoxazolyl, benzimidazolyl, indolyl, isoindolyl, pyrazinyl. diazinyl, pyrazine, triazinyltriazine, tetrazinyl, and tetrazolyl. When substituted the substituted group(s) is preferably one or more selected from alkyl, cycloalkyl, aryl, heteroaryl, heteroalicyclic, hydroxy, alkoxy, aryloxy, heteroaryloxy, heteroalicycloxy, thiohydroxy, thioaryloxy, thioheteroaryloxy, thioheteroalicycloxy, cyano, halogen, nitro, carbonyl, O-carbamyl, N-carbamyl, C-amido, N-amido, C-carboxy, O-carboxy, sulfinyl, sulfonyl, sulfonamido, trihalomethyl, ureido, amino, and —NR$^x$R$^y$, wherein R$^x$ and R$^y$ are as defined above.

As used herein, a "heteroalicyclic" group refers to a monocyclic or fused ring group having in the ring(s) one or more atoms selected from the group consisting of nitrogen, oxygen and sulfur. The rings may also have one or more double bonds. However, the rings do not have a completely conjugated pi-electron system. Examples, without limitation, of heteroalicyclic groups are azetidinyl, piperidyl, piperazinyl, imidazolinyl, thiazolidinyl, 3-pyrrolidin-1-yl, morpholinyl, thiomorpholinyl and tetrahydropyranyl. When substituted the substituted group(s) is preferably one or more selected from alkyl, cycloalkyl, aryl, heteroaryl, heteroalicyclic, hydroxy, alkoxy, aryloxy, heteroaryloxy, heteroalicycloxy, thiohydroxy, thioalkoxy, thioaryloxy, thioheteroaryloxy, thioheteroalicycloxy, cyano, halogen, nitro, carbonyl, thiocarbonyl, O-carbamyl, N-carbamyl, O-thiocarbamyl, N-thiocarbamyl, C-amido, C-thioamido, N-amido, C-carboxy, O-carboxy, sulfinyl, sulfonyl, sulfonamido, trihalomethanesulfonamido, trihalomethanesulfonyl, silyl, guanyl, guanidino, ureido, phosphonyl, amino and —NR$^x$R$^y$, wherein R$^x$ and R$^y$ are as defined above.

An "alkyl" group refers to a saturated aliphatic hydrocarbon including straight chain and branched chain groups. Preferably, the alkyl group has 1 to 20 carbon atoms (whenever a numerical range; e.g., "1-20", is stated herein, it means that the group, in this case the alkyl group may contain 1 carbon atom, 2 carbon atoms, 3 carbon atoms, etc. up to and including 20 carbon atoms). More preferably, it is a medium size alkyl having 1 to 10 carbon atoms. Most preferably, it is a lower alkyl having 1 to 4 carbon atoms. The alkyl group may be substituted or unsubstituted. When substituted, the substituent group(s) is preferably one or more individually selected from trihaloalkyl, cycloalkyl, aryl, heteroaryl, heteroalicyclic, hydroxy, alkoxy, aryloxy, heteroaryloxy, heteroalicycloxy, thiohydroxy, thioalkoxy, thioaryloxy, thioheteroaryloxy, thioheteroalicycloxy, cyano, halo, nitro, carbonyl, thiocarbonyl, O-carbamyl, N-carbamyl, O-thiocarbamyl, N-thiocarbamyl, C-amido, C-thioamido, N-amido, C-carboxy, O-carboxy, sulfinyl, sulfonyl, sulfonamido, trihalomethanesulfonamido, trihalomethanesulfonyl, and combined, a five- or six-member heteroalicyclic ring.

A "cycloalkyl" group refers to an all-carbon monocyclic or fused ring (i.e., rings which share and adjacent pair of carbon atoms) group wherein one or more rings does not have a completely conjugated pi-electron system. Examples, without limitation, of cycloalkyl groups are cyclopropane, cyclobutane, cyclopentane, cyclopentene, cyclohexane, cyclohexadiene, cycloheptane, cycloheptatriene and adamantane. A cycloalkyl group may be substituted or unsubstituted. When substituted, the substituent group(s) is preferably one or more individually selected from alkyl, aryl, heteroaryl, heteroalicyclic, hydroxy, alkoxy, aryloxy, heteroaryloxy, heteroalicycloxy, thiohydroxy, thioalkoxy, thioaryloxy, thioheteroaryloxy, thioheteroalicycloxy, cyano, halo, nitro, carbonyl, thiocarbonyl, O-carbamyl, N-carbamyl, O-thiocarbamyl, N-thiocarbamyl, C-amido, C-thioamido, N-amido, C-carboxy, O-carboxy, sulfinyl, sulfonyl, sulfonamido, trihalo-methanesulfonamido, trihalomethanesulfonyl, silyl, guanyl, guanidino, ureido, phosphonyl, amino and —NR$^x$R$^y$ with R$^x$ and R$^y$ as defined above.

An "alkenyl" group refers to an alkyl group, as defined herein, consisting of at least two carbon atoms and at least one carbon-carbon double bond.

An "alkynyl" group refers to an alkyl group, as defined herein, consisting of at least two carbon atoms and at least one carbon-carbon triple bond.

A "hydroxy" group refers to an —OH group.

An "alkoxy" group refers to both an —O-alkyl and an —O-cycloalkyl group as defined herein.

An "aryloxy" group refers to both an —O-aryl and an —O-heteroaryl group, as defined herein.

A "heteroaryloxy" group refers to a heteroaryl-O— group with heteroaryl as defined herein.

A "heteroalicycloxy" group refers to a heteroalicyclic-O— group with heteroalicyclic as defined herein.

A "thiohydroxy" group refers to an —SH group.

A "thioalkoxy" group refers to both an S-alkyl and an —S-cycloalkyl group, as defined herein.

A "thioaryloxy" group refers to both an —S-aryl and an —S-heteroaryl group, as defined herein.

A "thioheteroaryloxy" group refers to a heteroaryl-S— group with heteroaryl as defined herein.

A "thioheteroalicycloxy" group refers to a heteroalicyclic-S— group with heteroalicyclic as defined herein.

A "carbonyl" group refers to a —C(=O)—R" group, where R" is selected from the group consisting of hydrogen, alkyl, alkenyl, alkynyl, cycloalkyl, aryl, heteroaryl (bonded through a ring carbon) and heteroalicyclic (bonded through a ring carbon), as each is defined herein.

An "aldehyde" group refers to a carbonyl group where R" is hydrogen.

A "thiocarbonyl" group refers to a —C(=S)—R" group, with R" as defined herein.

A "Keto" group refers to a —CC(=O)C— group wherein the carbon on either or both sides of the C=O may be alkyl, cycloalkyl, aryl or a carbon of a heteroaryl or heteroaliacyclic group.

A "trihalomethanecarbonyl" group refers to a Z$_3$CC(=O)— group with said Z being a halogen.

A "C-carboxy" group refers to a —C(=O)O—R" groups, with R" as defined herein.

An "O-carboxy" group refers to a R"C(=O)O-group, with R" as defined herein.

A "carboxylic acid" group refers to a C-carboxy group in which R" is hydrogen.

A "trihalomethyl" group refers to a —CZ$_3$, group wherein Z is a halogen group as defined herein.

A "trihalomethanesulfonyl" group refers to an Z$_3$CS(=O)$_2$— groups with Z as defined above.

A "trihalomethanesulfonamido" group refers to a Z$_3$CS(=O)$_2$NR$^x$— group with Z and R$^x$ as defined herein.

A "sulfinyl" group refers to a —S(=O)—R" group, with R" as defined herein and, in addition, as a bond only; i.e., —S(O)—.

A "sulfonyl" group refers to a —S(=O)$_2$R" group with R" as defined herein and, in addition as a bond only; i.e., —S(O)$_2$—.

A "S-sulfonamido" group refers to a —S(=O)$_2$NR$^X$R$^Y$, with R$^X$ and R$^Y$ as defined herein.

A "N-Sulfonamido" group refers to a R"S(=O)$_2$NR$_X$— group with R$_x$ as defined herein.

A "O-carbamyl" group refers to a —OC(=O)NR$^x$R$^y$ as defined herein.

A "N-carbamyl" group refers to a R$^x$OC(=O)NR$^y$ group, with R$^x$ and R$^y$ as defined herein.

A "O-thiocarbamyl" group refers to a —OC(=S)NR$^x$R$^y$ group with R$^x$ and R$^y$ as defined herein.

A "N-thiocarbamyl" group refers to a R$^x$OC(=S)NR$^y$— group with R$^x$ and R$^y$ as defined herein.

An "amino" group refers to an —NH$_2$ group.

A "C-amido" group refers to a —C(=O)NR$^x$R$^y$ group with R$^x$ and R$^y$ as defined herein.

A "C-thioamido" group refers to a —C(=S)NR$^x$R$^y$ group, with R$^x$ and R$^y$ as defined herein.

A "N-amido" group refers to a R$^x$C(=O)NR$^y$— group, with R$^x$ and R$^y$ as defined herein.

An "ureido" group refers to a —NR$^x$C(=O)NR$^y$R$^{y2}$ group with R$^x$ and R$^y$ as defined herein and R$^{y2}$ defined the same as R$^x$ and R$^y$.

A "guanidino" group refers to a R$^x$NC(=N)NR$^y$R$^{y2}$ group, with R$^x$, R$^y$ and R$^{y2}$ as defined herein.

A "guanyl" group refers to a R$^x$R$^y$NC(=N)— group, with R$^x$ and R$^Y$ as defined herein.

A "cyano" group refers to a —CN group.

A "silyl" group refers to a —Si(R")$_3$, with R" as defined herein.

A "phosphonyl" group refers to a P(=O)(OR$^x$)$_2$ with R$^x$ as defined herein.

A "hydrazino" group refers to a —NR$^x$NR$^y$R$^{y2}$ group with R$^x$, R$^y$ and R$^{y2}$ as defined herein.

Any two adjacent R groups may combine to form an additional aryl, cycloalkyl, heteroaryl or heterocyclic ring fused to the ring initially bearing those R groups.

It is known in the art that nitrogen atoms in heteroaryl systems can be "participating in a heteroaryl ring double bond", and this refers to the form of double bonds in the two tautomeric structures which comprise five-member ring heteroaryl groups. This dictates whether nitrogens can be substituted as well understood by chemists in the art. The disclosure and claims of the present invention are based on the known general principles of chemical bonding. It is understood that the claims do not encompass structures known to be unstable or not able to exist based on the literature.

Physiologically acceptable salts and prodrugs of compounds disclosed herein are within the scope of this invention. The term "pharmaceutically acceptable salt" as used herein and in the claims is intended to include nontoxic base addition salts. Suitable salts include those derived from organic and inorganic acids such as, without limitation, hydrochloric acid, hydrobromic acid, phosphoric acid, sulfuric acid, methanesulfonic acid, acetic acid, tartaric acid, lactic acid, sulfinic acid, citric acid, maleic acid, fumaric acid, sorbic acid, aconitic acid, salicylic acid, phthalic acid, and the like. The term "pharmaceutically acceptable salt" as used herein is also intended to include salts of acidic groups, such as a carboxylate, with such counterions as ammonium, alkali metal salts, particularly sodium or potassium, alkaline earth metal salts, particularly calcium or magnesium, and salts with suitable organic bases such as lower alkylamines (methylamine, ethylamine, cyclohexylamine, and the like) or with substituted lower alkylamines (e.g. hydroxyl-substituted alkylamines such as diethanolamine, triethanolamine or tris(hydroxymethyl)-aminomethane), or with bases such as piperidine or morpholine.

In the method of the present invention, the term "antiviral effective amount" means the total amount of each active component of the method that is sufficient to show a meaningful patient benefit, i.e., healing of acute conditions characterized by inhibition of the HIV infection. When applied to an individual active ingredient, administered alone, the term refers to that ingredient alone. When applied to a combination, the term refers to combined amounts of the active ingredients that result in the therapeutic effect, whether administered in combination, serially or simultaneously. The terms "treat, treating, treatment" as used herein and in the claims means preventing or ameliorating diseases associated with HIV infection.

The present invention is also directed to combinations of the compounds with one or more agents useful in the treatment of AIDS. For example, the compounds of this invention may be effectively administered, whether at periods of pre-exposure and/or post-exposure, in combination with effective amounts of the AIDS antivirals, immunomodulators, antiinfectives, or vaccines, such as those in the following table.

| Drug Name | Manufacturer | Indication |
|---|---|---|
| ANTIVIRALS | | |
| 097 | Hoechst/Bayer | HIV infection, AIDS, ARC (non-nucleoside reverse transcriptase (RT) inhibitor) |
| Amprenivir 141 W94 GW 141 | Glaxo Wellcome | HIV infection, AIDS, ARC (protease inhibitor) |
| Abacavir (1592U89) GW 1592 | Glaxo Wellcome | HIV infection, AIDS, ARC (RT inhibitor) |
| Acemannan | Carrington Labs (Irving, TX) | ARC |
| Acyclovir | Burroughs Wellcome | HIV infection, AIDS, ARC, in combination with AZT |
| AD-439 | Tanox Biosystems | HIV infection, AIDS, ARC |
| AD-519 | Tanox Biosystems | HIV infection, AIDS, ARC |
| Adefovir dipivoxil | Gilead Sciences | HIV infection |
| AL-721 | Ethigen (Los Angeles, CA) | ARC, PGL HIV positive, AIDS |
| Alpha Interferon | Glaxo Wellcome | Kaposi's sarcoma, HIV in combination w/Retrovir |
| Ansamycin LM 427 | Adria Laboratories (Dublin, OH) Erbamont (Stamford, CT) | ARC |
| Antibody which Neutralizes pH Labile alpha aberrant Interferon | Advanced Biotherapy Concepts (Rockville, MD) | AIDS, ARC |
| AR177 | Aronex Pharm | HIV infection, AIDS, ARC |
| Beta-fluoro-ddA | Nat'l Cancer Institute | AIDS-associated diseases |
| BMS-232623 (CGP-73547) | Bristol-Myers Squibb/ Novartis | HIV infection, AIDS, ARC (protease inhibitor) |
| BMS-234475 (CGP-61755) | Bristol-Myers Squibb/ Novartis | HIV infection, AIDS, ARC (protease inhibitor) |
| CI-1012 | Warner-Lambert | HIV-1 infection |
| Cidofovir | Gilead Science | CMV retinitis, herpes, papillomavirus |
| Curdlan sulfate | AJI Pharma USA | HIV infection |
| Cytomegalovirus Immune globin | MedImmune | CMV retinitis |
| Cytovene Ganciclovir | Syntex | Sight threatening CMV peripheral CMV retinitis |
| Delaviridine | Pharmacia-Upjohn | HIV infection, AIDS, ARC (RT inhibitor) |
| Dextran Sulfate | Ueno Fine Chem. Ind. Ltd. (Osaka, Japan) | AIDS, ARC, HIV positive asymptomatic |
| ddC Dideoxycytidine | Hoffman-La Roche | HIV infection, AIDS, ARC |
| ddI Dideoxyinosine | Bristol-Myers Squibb | HIV infection, AIDS, ARC; combination with AZT/d4T |
| DMP-450 | AVID (Camden, NJ) | HIV infection, AIDS, ARC (protease inhibitor) |
| Efavirenz (DMP 266) (−)6-Chloro-4-(S)-cyclopropylethynyl-4(S)-trifluoro-methyl-1,4-dihydro-2H-3,1-benzoxazin-2-one, STOCRINE | DuPont Merck | HIV infection, AIDS, ARC (non-nucleoside RT inhibitor) |
| EL10 | Elan Corp, PLC (Gainesville, GA) | HIV infection |
| Famciclovir | Smith Kline | herpes zoster, herpes simplex |
| FTC | Emory University | HIV infection, AIDS, ARC (reverse transcriptase inhibitor) |
| GS 840 | Gilead | HIV infection, AIDS, ARC (reverse transcriptase inhibitor) |
| HBY097 | Hoechst Marion Roussel | HIV infection, AIDS, ARC (non-nucleoside reverse transcriptase inhibitor) |
| Hypericin | VIMRx Pharm. | HIV infection, AIDS, ARC |
| Recombinant Human Interferon Beta | Triton Biosciences (Almeda, CA) | AIDS, Kaposi's sarcoma, ARC |
| Interferon alfa-n3 | Interferon Sciences | ARC, AIDS |
| Indinavir | Merck | HIV infection, AIDS, ARC, asymptomatic HIV positive, also in combination with AZT/ddI/ddC |
| ISIS 2922 | ISIS Pharmaceuticals | CMV retinitis |
| KNI-272 | Nat'l Cancer Institute | HIV-assoc. diseases |
| Lamivudine, 3TC | Glaxo Wellcome | HIV infection, AIDS, ARC (reverse transcriptase inhibitor); also with AZT |
| Lobucavir | Bristol-Myers Squibb | CMV infection |
| Nelfinavir | Agouron Pharmaceuticals | HIV infection, AIDS, ARC |

-continued

| Drug Name | Manufacturer | Indication |
|---|---|---|
| Nevirapine | Boeheringer Ingleheim | (protease inhibitor) HIV infection, AIDS, ARC (RT inhibitor) |
| Novapren | Novaferon Labs, Inc. (Akron, OH) | HIV inhibitor |
| Peptide T Octapeptide Sequence | Peninsula Labs (Belmont, CA) | AIDS |
| Trisodium Phosphonoformate | Astra Pharm. Products, Inc. | CMV retinitis, HIV infection, other CMV infections |
| PNU-140690 | Pharmacia Upjohn | HIV infection, AIDS, ARC (protease inhibitor) |
| Probucol | Vyrex | HIV infection, AIDS |
| RBC-CD4 | Sheffield Med. Tech (Houston, TX) | HIV infection, AIDS, ARC |
| Ritonavir | Abbott | HIV infection, AIDS, ARC (protease inhibitor) |
| Saquinavir | Hoffmann-LaRoche | HIV infection, AIDS, ARC (protease inhibitor) |
| Stavudine; d4T Didehydrodeoxy-thymidine | Bristol-Myers Squibb | HIV infection, AIDS, ARC |
| Valaciclovir | Glaxo Wellcome | Genital HSV & CMV infections |
| Virazole Ribavirin | Viratek/ICN (Costa Mesa, CA) | asymptomatic HIV positive, LAS, ARC |
| VX-478 | Vertex | HIV infection, AIDS, ARC |
| Zalcitabine | Hoffmann-LaRoche | HIV infection, AIDS, ARC, with AZT |
| Zidovudine; AZT | Glaxo Wellcome | HIV infection, AIDS, ARC, Kaposi's sarcoma, in combination with other therapies |
| IMMUNOMODULATORS | | |
| AS-101 | Wyeth-Ayerst | AIDS |
| Bropirimine | Pharmacia Upjohn | Advanced AIDS |
| Acemannan | Carrington Labs, Inc. (Irving, TX) | AIDS, ARC |
| CL246,738 | American Cyanamid Lederle Labs | AIDS, Kaposi's sarcoma |
| EL10 | Elan Corp, PLC (Gainesville, GA) | HIV infection |
| FP-21399 | Fuki ImmunoPharm | Blocks HIV fusion with CD4+ cells |
| Gamma Interferon | Genentech | ARC, in combination w/TNF (tumor necrosis factor) |
| Granulocyte Macrophage Colony Stimulating Factor | Genetics Institute Sandoz | AIDS |
| Granulocyte Macrophage Colony Stimulating Factor | Hoechst-Roussel Immunex | AIDS |
| Granulocyte Macrophage Colony Stimulating Factor | Schering-Plough | AIDS, combination w/AZT |
| HIV Core Particle Immunostimulant | Rorer | Seropositive HIV |
| IL-2 Interleukin-2 | Cetus | AIDS, in combination w/AZT |
| IL-2 Interleukin-2 | Hoffman-LaRoche Immunex | AIDS, ARC, HIV, in combination w/AZT |
| IL-2 Interleukin-2 (aldesiukin) | Chiron | AIDS, increase in CD4 cell counts |
| Immune Globulin Intravenous (human) | Cutter Biological (Berkeley, CA) | Pediatric AIDS, in combination w/AZT |
| IMREG-1 | Imreg | AIDS, Kaposi's sarcoma, ARC, PGL |
| IMREG-2 | (New Orleans, LA) Imreg (New Orleans, LA) | AIDS, Kaposi's sarcoma, ARC, PGL |
| Imuthiol Diethyl Dithio Carbamate | Merieux Institute | AIDS, ARC |
| Alpha-2 Interferon | Schering Plough | Kaposi's sarcoma w/AZT, AIDS |
| Methionine-Enkephalin | TNI Pharmaceutical (Chicago, IL) | AIDS, ARC |
| MTP-PE Muramyl-Tripeptide | Ciba-Geigy Corp. | Kaposi's sarcoma |
| Granulocyte Colony Stimulating Factor | Amgen | AIDS, in combination w/AZT |
| Remune | Immune Response Corp. | Immunotherapeutic |
| rCD4 Recombinant Soluble Human CD4 | Genentech | AIDS, ARC |
| rCD4-IgG hybrids | | AIDS, ARC |
| Recombinant Soluble Human CD4 | Biogen | AIDS, ARC |
| Interferon Alfa 2a | Hoffman-La Roche | Kaposi's sarcoma AIDS, ARC, in combination w/AZT |
| SK&F106528 Soluble T4 | Smith Kline | HIV infection |
| Thymopentin | Immunobiology Research Institute (Annandale, NJ) | HIV infection |
| Tumor Necrosis Factor; TNF | Genentech | ARC, in combination w/gamma Interferon |
| ANTI-INFECTIVES | | |
| Clindamycin with Primaquine | Pharmacia Upjohn | PCP |
| Fluconazole | Pfizer | Cryptococcal meningitis, candidiasis |
| Pastille Nystatin Pastille | Squibb Corp. | Prevention of oral candidiasis |
| Ornidyl Eflornithine | Merrell Dow | PCP |
| Pentamidine Isethionate (IM & IV) | LyphoMed (Rosemont, IL) | PCP treatment |
| Trimethoprim | | Antibacterial |
| Trimethoprim/sulfa | | Antibacterial |
| Piritrexim | Burroughs Wellcome | PCP treatment |
| Pentamidine Isethionate for Inhalation | Fisons Corporation | PCP prophylaxis |
| Spiramycin | Rhone-Poulenc | Cryptosporidial diarrhea |
| Intraconazole-R51211 | Janssen-Pharm. | Histoplasmosis; cryptococcal meningitis |
| Trimetrexate | Warner-Lambert | PCP |
| Daunorubicin | NeXstar, Sequus | Kaposi's sarcoma |
| Recombinant Human Erythropoietin | Ortho Pharm. Corp. | Severe anemia assoc. with AZT therapy |
| Recombinant Human Growth Hormone | Serono | AIDS-related wasting, cachexia |
| Megestrol Acetate | Bristol-Myers Squibb | Treatment of anorexia assoc. W/AIDS |
| Testosterone | Alza, Smith Kline | AIDS-related wasting |
| Total Enteral Nutrition | Norwich Eaton Pharmaceuticals | Diarrhea and malabsorption related to AIDS |

Additionally, the compounds of the invention herein may be used in combination with another class of agents for treating AIDS which are called HIV entry inhibitors. Examples of such HIV entry inhibitors are discussed in DRUGS OF THE FUTURE 1999, 24(12), pp. 1355-1362; CELL, Vol. 9, pp. 243-246, Oct. 29, 1999; and DRUG DISCOVERY TODAY, Vol. 5, No. 5, May 2000, pp. 183-194.

It will be understood that the scope of combinations of the compounds of this invention with AIDS antivirals, immunomodulators, anti-infectives, HIV entry inhibitors or vaccines is not limited to the list in the above Table, but includes in principle any combination with any pharmaceutical composition useful for the treatment of AIDS.

Preferred combinations are simultaneous or alternating treatments of with a compound of the present invention and an inhibitor of HIV protease and/or a non-nucleoside inhibitor of HIV reverse transcriptase. An optional fourth component in the combination is a nucleoside inhibitor of HIV reverse transcriptase, such as AZT, 3TC, ddC or ddI. A preferred inhibitor of HIV protease is indinavir, which is the sulfate salt of N-(2(R)-hydroxy-1-(S)-indanyl)-2(R)-phenylmethyl-4-(S)-hydroxy-5-(1-(4-(3-pyridyl-methyl)-2(S)—N'-(t-butyl-carboxamido)-piperazinyl))-pentaneamide ethanolate, and is synthesized according to U.S. Pat. No. 5,413,999. Indinavir is generally administered at a dosage of 800 mg three times a day. Other preferred protease inhibitors are nelfinavir and ritonavir. Another preferred inhibitor of HIV protease is saquinavir which is administered in a dosage of 600 or 1200 mg tid. Preferred non-nucleoside inhibitors of HIV reverse transcriptase include efavirenz. The preparation of ddC, ddI and AZT are also described in EPO 0,484,071. These combinations may have unexpected effects on limiting the spread and degree of infection of HIV. Preferred combinations include those with the following (1) indinavir with efavirenz, and, optionally, AZT and/or 3TC and/or ddI and/or ddC; (2) indinavir, and any of AZT and/or ddI and/or ddC and/or 3TC, in particular, indinavir and AZT and 3TC; (3) stavudine and 3TC and/or zidovudine; (4) zidovudine and lamivudine and 141W94 and 1592U89; (5) zidovudine and lamivudine.

In such combinations the compound of the present invention and other active agents may be administered separately or in conjunction. In addition, the administration of one element may be prior to, concurrent to, or subsequent to the administration of other agent(s).

Abbreviations

The following abbreviations, most of which are conventional abbreviations well known to those skilled in the art, are used throughout the description of the invention and the examples. Some of the abbreviations used are as follows:
h=hour(s)
rt=room temperature
mol=mole(s)
mmol=millimole(s)
g=gram(s)
mg=milligram(s)
mL=milliliter(s)
TFA=Trifluoroacetic Acid
DCE=1,2-Dichloroethane
CH$_2$Cl$_2$=Dichloromethane
TPAP=tetrapropylammonium perruthenate
THF=Tetrahydrofuran
DEPBT=3-(Diethoxyphosphoryloxy)-1,2,3-benzotriazin-4(3H)-one
DMAP=4-dimethylaminopyridine
P-EDC=Polymer supported 1-(3-dimethylaminopropyl)-3-ethylcarbodiimide
EDC=1-(3-dimethylaminopropyl)-3-ethylcarbodiimide
DMF=N,N-dimethylformamide
Hunig's Base=N,N-Diisopropylethylamine
mCPBA=meta-Chloroperbenzoic Acid
azaindole=1H-Pyrrolo-pyridine
4-azaindole=1H-pyrrolo[3,2-b]pyridine
5-azaindole=1H-Pyrrolo[3,2-c]pyridine
6-azaindole=1H-pyrrolo[2,3-c]pyridine
7-azaindole=1H-Pyrrolo[2,3-b]pyridine
PMB=4-Methoxybenzyl
DDQ=2,3-Dichloro-5,6-dicyano-1,4-benzoquinone
OTf=Trifluoromethanesulfonoxy
NMM=4-Methylmorpholine
PIP-COPh=1-Benzoylpiperazine
NaHMDS=Sodium hexamethyldisilazide
EDAC=1-(3-Dimethylaminopropyl)-3-ethylcarbodiimide
TMS=Trimethylsilyl
DCM=Dichloromethane
DCE=Dichloroethane
MeOH=Methanol
THF=Tetrahydrofuran
EtOAc=Ethyl Acetate
LDA=Lithium diisopropylamide
TMP-Li=2,2,6,6-tetramethylpiperidinyl lithium
DME=Dimethoxyethane
DIBALH=Diisobutylaluminum hydride
HOBT 11-hydroxybenzotriazole
CBZ=Benzyloxycarbonyl
PCC=Pyridinium chlorochromate Chemistry The present invention comprises compounds of Formula I, their pharmaceutical formulations, and their use in patients suffering from or susceptible to HIV infection. The compounds of Formula I include pharmaceutically acceptable salts thereof.

The synthesis procedures and anti-HIV-1 activities of indoleoxoacetic pyrrolidine containing analogs are below. Procedures for making Z are described herein or in many cases references of Blair, Wang, Wallace, references 93-95 respectively.

Additional general procedures to construct substituted azaindole Q and Z of Formula I and intermediates useful for their synthesis are described in the following Schemes 1-16.

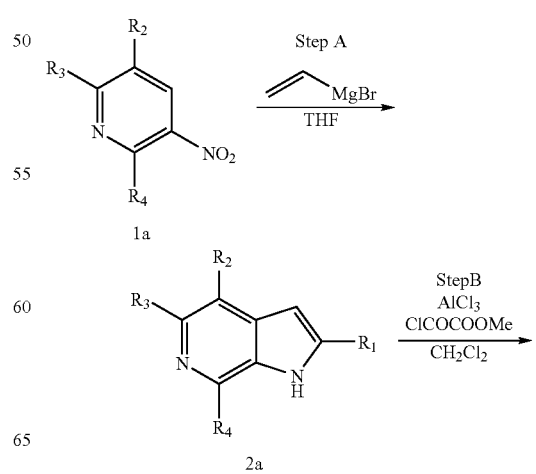

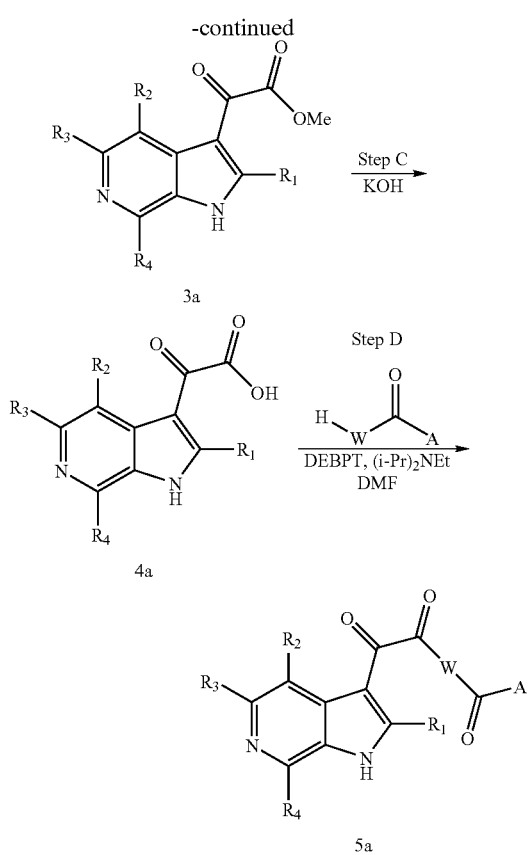

Step A in Scheme 1 depicts the synthesis of an aza indole intermediate, 2, via the well known Bartoli reaction in which vinyl magnesium bromide reacts with an aryl or heteroaryl nitro group, such as in 1, to form a five-membered nitrogen containing ring as shown. Some references for the above transformation include: Bartoli et al. a) *Tetrahedron Lett.* 1989, 30, 2129. b) *J. Chem. Soc. Perkin Trans.* 1 1991, 2757. c) *J. Chem. Soc. Perkin Trans. II* 1991, 657. d) Synthesis (1999), 1594. In the preferred procedure, a solution of vinyl Magnesium bromide in THF (typically 1.0M but from 0.25 to 3.0M) is added dropwise to a solution of the nitro pyridine in THF at −78° under an inert atmosphere of either nitrogen or Argon. After addition is completed, the reaction temperature is allowed to warm to −20° and then is stirred for approximately 12 h before quenching with 20% aq ammonium chloride solution. The reaction is extracted with ethyl acetate and then worked up in a typical manner using a drying agent such as anhydrous magnesium sulfate or sodium sulfate. Products are generally purified using chromatography over Silica gel. Best results are generally achieved using freshly prepared vinyl Magnesium bromide. In some cases, vinyl Magnesium chloride may be substituted for vinyl Magnesium bromide.

Substituted azaindoles may be prepared by methods described in the literature or may be available from commercial sources. Thus there are many methods for carrying out step A in the literature and the specific examples are too numerous to even list. A review on the synthesis of 7-azaindoles has been published (Merour et. al. reference 102). Alternative syntheses of aza indoles and general methods for carrying out step A include, but are not limited to, those described in the following references (a-k below): a) Prokopov, A. A.; Yakhontov, L. N. *Khim.-Farm. Zh.* 1994, 28(7), 30-51; b) Lablache-Combier, A. Heteroaromatics. Photoinduced Electron Transfer 1988, Pt. C, 134-312; c) Saify, Zafar Said. Pak. *J. Pharmacol.* 1986, 2(2), 43-6; d) Bisagni, E. *Jerusalem Symp. Quantum Chem. Biochem.* 1972, 4, 439-45; e) Yakhontov, L. N. *Usp. Khim.* 1968, 37(7), 1258-87; f) Willette, R. E. *Advan. Heterocycl. Chem.* 1968, 9, 27-105; g) Mahadevan, I.; Rasmussen, M. *Tetrahedron* 1993, 49(33), 7337-52; h) Mahadevan, I.; Rasmussen, M. J. *Heterocycl. Chem.* 1992, 29(2), 359-67; i) Spivey, A. C.; Fekner, T.; Spey, S. E.; Adams, H. *J. Org. Chem.* 1999, 64(26), 9430-9443; j) Spivey, A. C.; Fekner, T.; Adams, H. *Tetrahedron Lett.* 1998, 39(48), 8919-8922; k) Advances in Heterocyclic Chemistry (Academic press) 1991, Vol. 52, pg 235-236 and references therein.

Step B. Intermediate 3 can be prepared by reaction of aza-indole, intermediate 2, with an excess of ClCOCOOMe in the presence of AlCl$_3$ (aluminum chloride) (Sycheva et al, Ref. 26, Sycheva, T. V.; Rubtsov, N. M.; Sheinker, Yu. N.; Yakhontov, L. N. Some reactions of 5-cyano-6-chloro-7-azaindoles and lactam-lactim tautomerism in 5-cyano-6-hydroxy-7-azaindolines. *Khim. Geterotsikl. Soedin.,* 1987, 100-106). Typically an inert solvent such as CH$_2$Cl$_2$ is used but others such as THF, Et$_2$O, DCE, dioxane, benzene, or toluene may find applicability either alone or in mixtures. Other oxalate esters such as ethyl or benzyl mono esters of oxalic acid could also suffice for either method shown above. More lipophilic esters ease isolation during aqueous extractions. Phenolic or substituted phenolic (such as pentafluorophenol) esters enable direct coupling of the HW(C=O)A group, such as a piperazine, in Step D without activation. Lewis acid catalysts, such as tin tetrachloride, titanium IV chloride, and aluminum chloride are employed in Step B with aluminum chloride being most preferred. Alternatively, the azaindole is treated with a Grignard reagent such as MeMgI (methyl magnesium iodide), methyl magnesium bromide or ethyl magnesium bromide and a zinc halide, such as ZnCl$_2$ (zinc chloride) or zinc bromide, followed by the addition of an oxalyl chloride mono ester, such as ClCOCOOMe (methyl chlorooxoacetate) or another ester as above, to afford the aza-indole glyoxyl ester (Shadrina et al, Ref. 25). Oxalic acid esters such as methyl oxalate, ethyl oxalate or as above are used. Aprotic solvents such as CH$_2$Cl$_2$, Et$_2$O, benzene, toluene, DCE, or the like may be used alone or in combination for this sequence. In addition to the oxalyl chloride mono esters, oxalyl chloride itself may be reacted with the azaindole and then further reacted with an appropriate amine, such as a piperazine derivative (See Scheme 52, for example).

Step C. Hydrolysis of the methyl ester, (intermediate 3, Scheme 1) affords a potassium salt of intermediate 4, which is coupled with mono-benzoylated piperazine derivatives as shown in Step D of Scheme 1. Some typical conditions employ methanolic or ethanolic sodium hydroxide followed by careful acidification with aqueous hydrochloric acid of varying molarity but 1M HCl is preferred. The acidification is not utilized in many cases as described above for the preferred conditions. Lithium hydroxide or potassium hydroxide could also be employed and varying amounts of water could be added to the alcohols. Propanols or butanols could also be used as solvents. Elevated temperatures up to the boiling points of the solvents may be utilized if ambient temperatures do not suffice. Alternatively, the hydrolysis may be carried out in a non polar solvent such as CH$_2$Cl$_2$ or THF in the presence of Triton B. Temperatures of −78° C. to the boiling point of the solvent may be employed but −10° C. is preferred. Other conditions for ester hydrolysis are listed in reference 41 and both this reference and many of the conditions for ester hydrolysis are well known to chemists of average skill in the art.

Alternative Procedures for Step B and C:

Imidazolium Chloroaluminate:

We found that ionic liquid 1-alkyl-3-alkylimidazolium chloroaluminate is generally useful in promoting the Friedel-Crafts type acylation of indoles and azaindoles. The ionic liquid is generated by mixing 1-alkyl-3-alkylimidazolium chloride with aluminium chloride at room temperature with vigorous stirring. 1:2 or 1:3 molar ratio of 1-alkyl-3-alkylimidazolium chloride to aluminium chloride is preferred. One particular useful imidazolium chloroaluminate for the acylation of azaindole with methyl or ethyl chlorooxoacetate is the 1-ethyl-3-methylimidazolium chloroaluminate. The reaction is typically performed at ambient temperature and the azaindoleglyoxyl ester can be isolated. More conveniently, we found that the glyoxyl ester can be hydrolyzed in situ at ambient temperature on prolonged reaction time (typically overnight) to give the corresponding glyoxyl acid for amide formation (Scheme 2).

Scheme 2

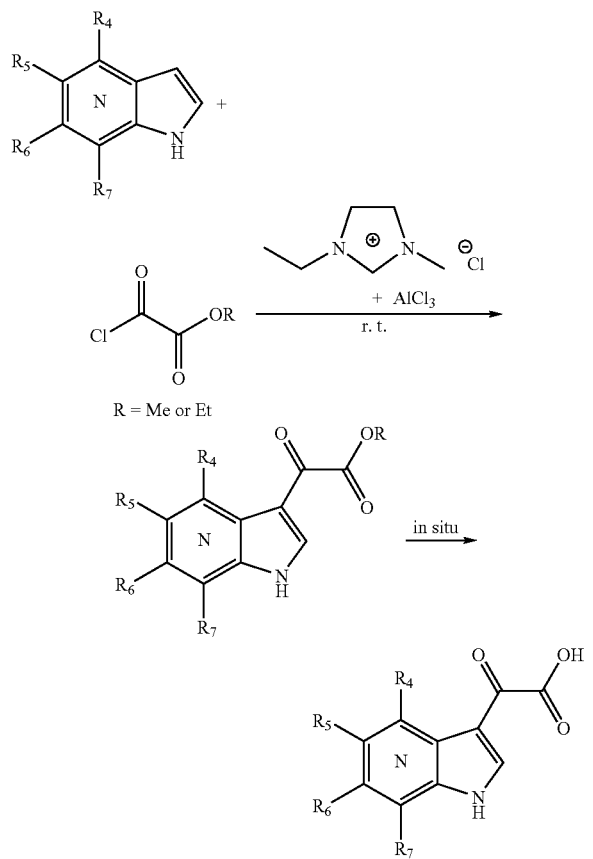

A representative experimental procedure is as follows: 1-ethyl-3-methylimidazolium chloride (2 equiv.; purchased from TCI; weighted under a stream of nitrogen) was stirred in an oven-dried round bottom flask at r.t. under a nitrogen atmosphere, and added aluminium chloride (6 equiv.; anhydrous powder packaged under argon in ampules purchased from Aldrich preferred; weighted under a stream of nitrogen). The mixture was vigorously stirred to form a liquid, which was then added azaindole (1 equiv.) and stirred until a homogenous mixture resulted. The reaction mixture was added dropwise ethyl or methyl chlorooxoacetate (2 equiv.) and then stirred at r.t. for 16 h. After which time, the mixture was cooled in an ice-water bath and the reaction quenched by carefully adding excess water. The precipitates were filtered, washed with water and dried under high vacuum to give the azaindoleglyoxyl acid. For some examples, 3 equivalents of 1-ethyl-3-methylimidazolium chloride and chlorooxoacetate may be required.

Related references: (1) Welton, T. *Chem. Rev.* 1999, 99, 2071; (2) Surette, J. K. D.; Green, L.; Singer, R. D. *Chem. Commun.* 1996, 2753; (3) Saleh, R. Y. WO 0015594.

Step D. The acid intermediate, 4, from step C of Scheme 1 is coupled with an amine A(C=O)WH preferably in the presence of DEPBT (3-(diethoxyphosphoryloxy)-1,2,3-benzotriazin-4(3H)-one) and N,N-diisopropylethylamine, commonly known as Hunig's base, to provide azaindole piperazine diamides. DEPBT was prepared according to the procedure of Ref. 28, Li, H.; Jiang, X.; Ye, Y.-H.; Fan, C.; Romoff, T.; Goodman, M. *Organic Lett.*, 1999, 1, 91-93. Typically an inert solvent such as DMF or THF is used but other aprotic solvents could be used. The group W as referred to herein is described below.

The amide bond construction reaction could be carried out using the preferred conditions described above, the EDC conditions described below, other coupling conditions described in this application, or alternatively by applying the conditions or coupling reagents for amide bond construction described later in this application for construction of substituents $R_1$-$R_4$. Some specific nonlimiting examples are given in this application.

It should be noted that in many cases reactions are depicted for only one position of an intermediate, such as the $R^5$ position, for example. It is to be understood that such reactions could be used at other positions, such as $R^2$-$R^4$, of the various intermediates. Reaction conditions and methods given in the specific examples are broadly applicable to compounds with other substitution and other transformations in this application. Schemes 1 and 2 describe general reaction schemes for taking appropriately substituted Q (indoles and azaindoles) and converting them to compounds of Formula I. While these schemes are very general, other permutations such as carrying a precursor or precursors to substituents $R^2$ through $R^5$ through the reaction scheme and then converting it to a compound of Formula I in the last step are also contemplated methods of this invention. Nonlimiting examples of such strategies follow in subsequent schemes.

Scheme 3

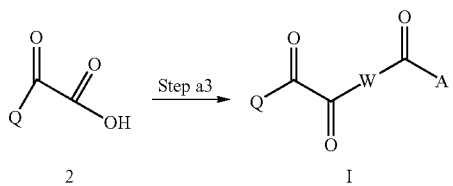

The amide coupling with amine H—W—C(O)A is shown in Scheme 3, step a3. The group W as referred to herein is either

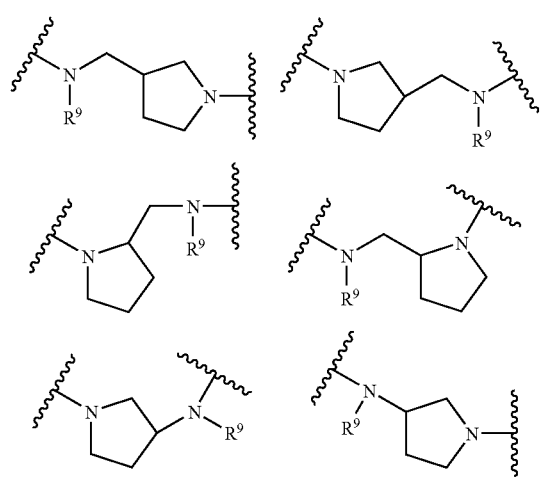

One preferred method for carrying out this reaction is the use of the peptide coupling reagent 3-(diethoxyphosphoryloxy)-1,2,3-benzotriazin-4(3H)-one (DEPBT) and an amine H—W—C(O)A in DMF solvent containing a tertiary amine such as N,N-diisopropylethylamine. Commonly used amide bond coupling conditions, e.g. EDC with HOBT or DMAP, are also employed in some examples. Typical stoichiometries are given in the specific examples but these ratios may be modified.

The amide bond construction reactions depicted in step a3 or step a5 of Schemes 3 and 4 respectively could be carried out using the specialized conditions described herein or alternatively by applying the conditions or coupling reagents for amide bond construction described in Wallace, reference 95. Some specific nonlimiting examples are given in this application.

Additional procedures for synthesizing, modifying and attaching groups WC(O)-A are contained in references 93-95 or described below except that the piperazine intermediates are replaced by the pyrrolidines described herein.

Scheme 4

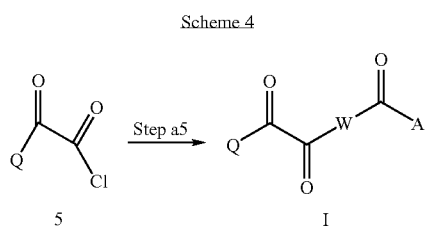

Scheme 4a

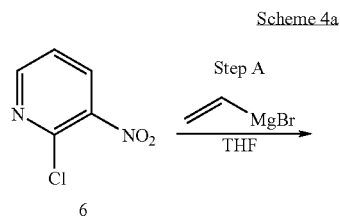

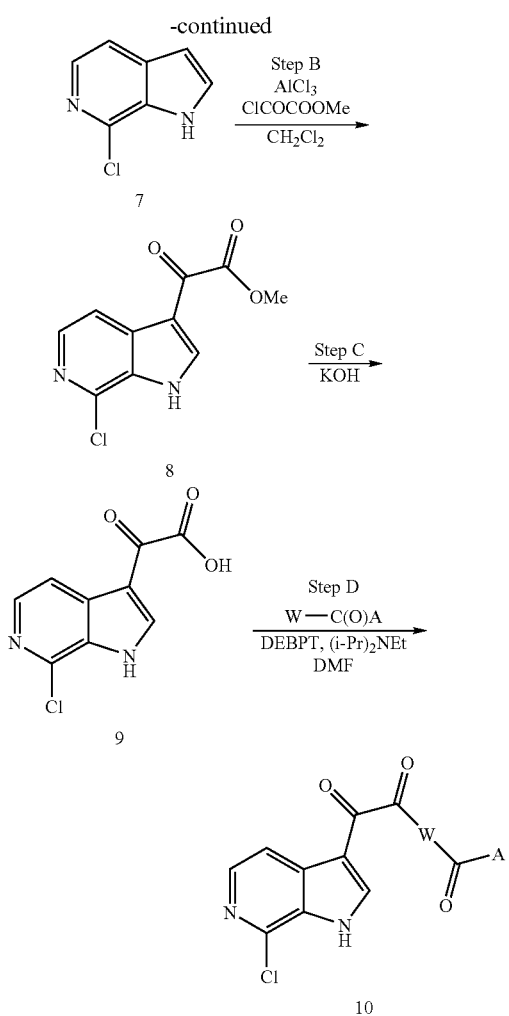

Scheme 4a provides a more specific example of the transformations previously described in Scheme 1. Intermediates 6-10 are prepared by the methodologies as described for intermediates 1a-5a in Scheme 1. Scheme 5 is another embodiment of the transformations described in Schemes 1 and 4a. Conversion of the phenol to the chloride (Step S, Scheme 5) may be accomplished according to the procedures described in Reimann, E.; Wichmann, P.; Hoefner, G.; Sci. Pharm. 1996, 64(3), 637-646; and Katritzky, A. R.; Rachwal, S.; Smith, T. P.; Steel, P. J.; J. Heterocycl. Chem. 1995, 32(3), 979-984. Step T of Scheme 5 can be carried out as described for Step A of Scheme 3. The bromo intermediate can then be converted into alkoxy, chloro, or fluoro intermediates as shown in Step U of Scheme 5. Scheme 2A describes the preferred method for preparing intermediate 6c or other closely related compounds containing a 4 methoxy group in the 6-azaindole system. When step U is the conversion of the bromide into alkoxy derivatives, the conversion may be carried out by reacting the bromide with an excess of sodium methoxide in methanol with cuprous salts, such as copper I bromide, copper I iodide, and copper I cyanide. The temperature may be carried out at temperatures of between ambient and 175° but most likely will be around 115° C. or 100° C. The reaction may be run in a pressure vessel or sealed tube to prevent escape of volatiles such as methanol. The preferred conditions utilize 3 eq of sodium methoxide in methanol, CuBr as the reaction catalyst (0.2 to 3 equivalents with the preferred being 1 eq or less), and a reaction temperature of 115° C. The reaction is carried out in a sealed tube or sealed reaction vessel. The conversion of the bromide into alkoxy derivatives may also be carried out according to procedures described in Palucki, M.; Wolfe, J. P.; Buchwald, S. L.; *J. Am. Chem. Soc.* 1997, 119(14), 3395-3396; Yamato, T.; Komine, M.; Nagano, Y.; *Org. Prep. Proc. Int.* 1997, 29(3), 300-303; Rychnovsky, S. D.; Hwang, K.; *J. Org. Chem.* 1994, 59(18), 5414-5418. Conversion of the bromide to the fluoro derivative (Step U, Scheme 2A) may be accomplished according to Antipin, I. S.; Vigalok, A. I.; Konovalov, A. I.; *Zh. Org. Khim.* 1991, 27(7), 1577-1577; and Uchibori, Y.; Umeno, M.; Seto, H.; Qian, Z.; Yoshioka, H.; *Synlett.* 1992, 4, 345-346. Conversion of the bromide to the chloro derivative (Step U, Scheme 2A) may be accomplished according to procedures described in Gilbert, E. J.; Van Vranken, D. L.; *J. Am. Chem. Soc.* 1996, 118(23), 5500-5501; Mongin, F.; Mongin, O.; Trecourt, F.; Godard, A.; Queguiner, G.; *Tetrahedron Lett.* 1996, 37(37), 6695-6698; and O'Connor, K. J.; Burrows, C. J.; *J. Org. Chem.* 1991, 56(3), 1344-1346. Steps V, W and X of Scheme 2A are carried out according to the procedures previously described for Steps B, C, and D of Scheme 1, respectively. The steps of Scheme 5 may be carried out in a different order as shown in Scheme 6 and Scheme 7.

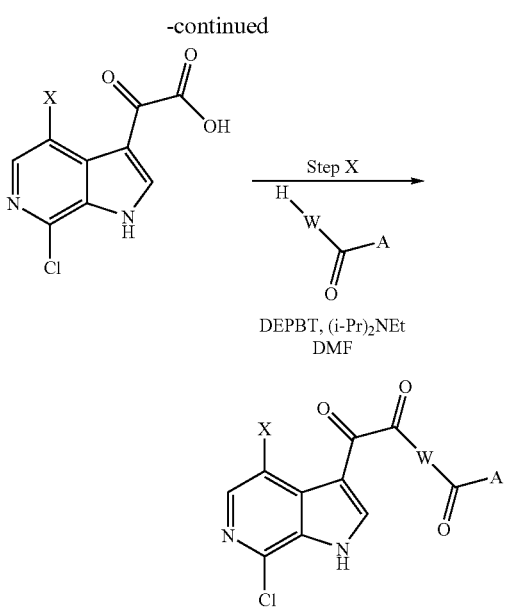

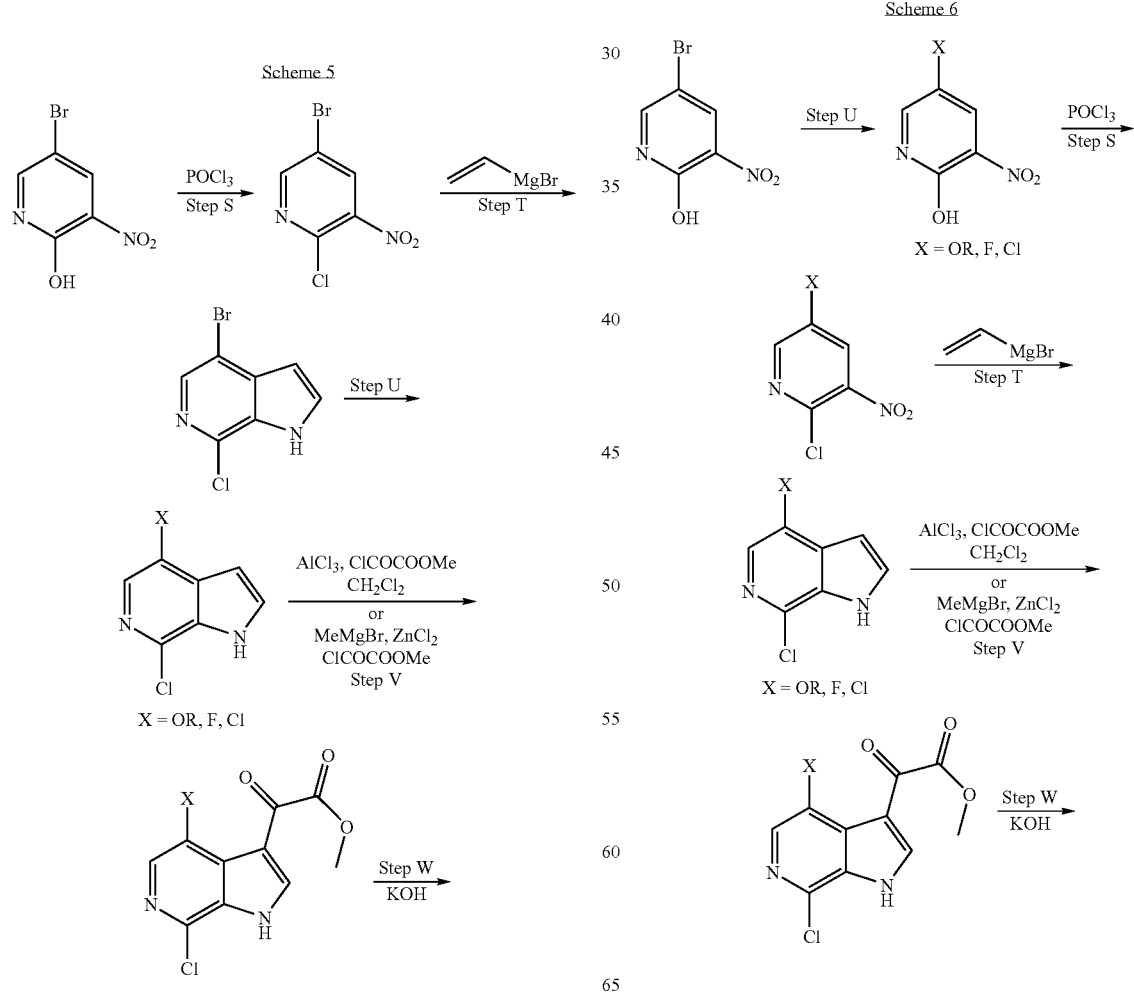

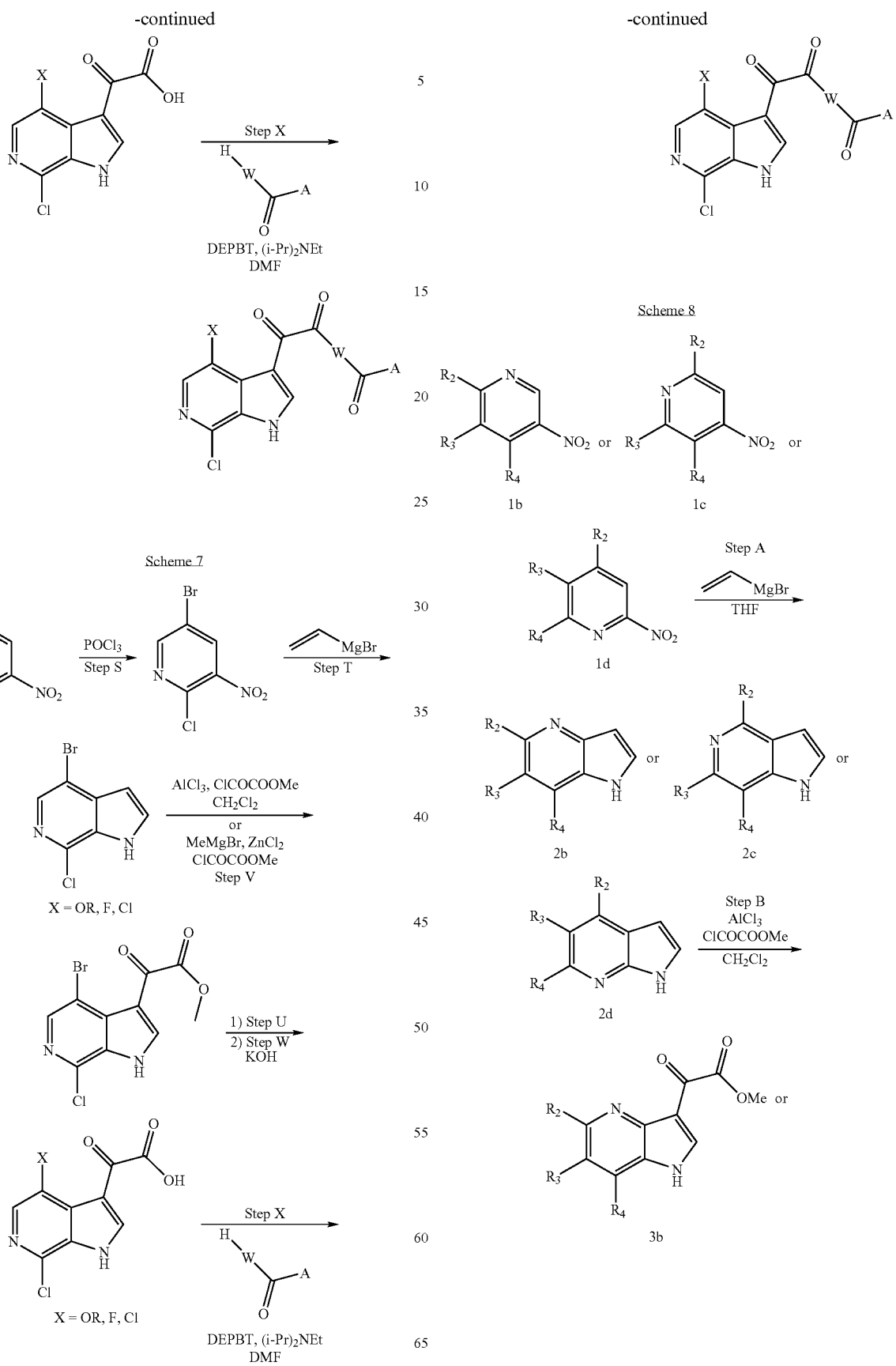

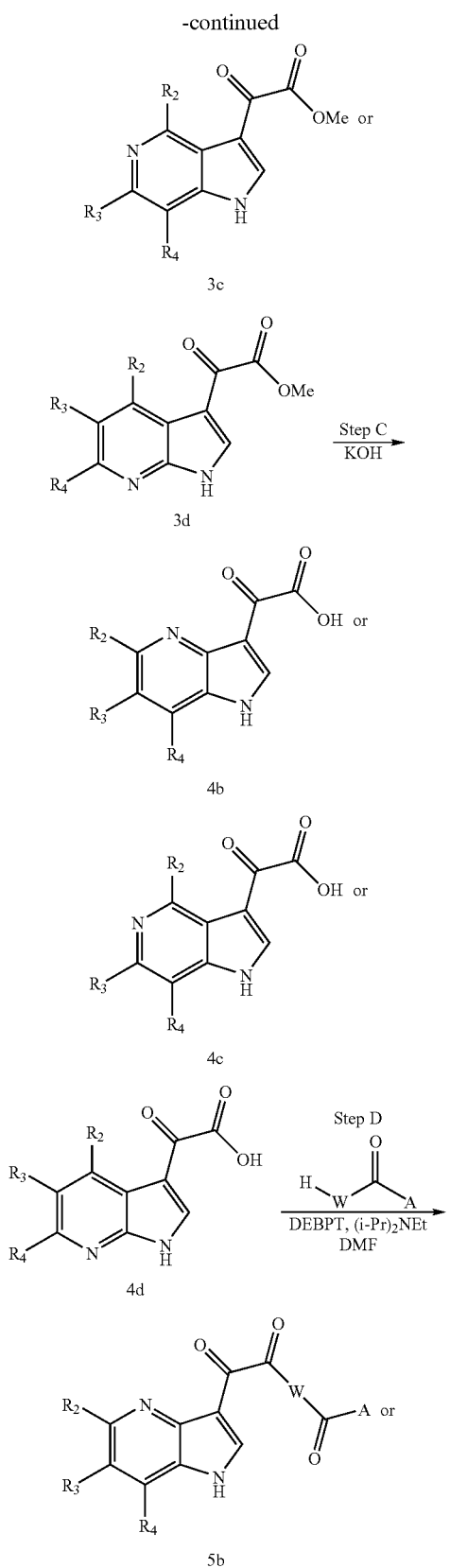

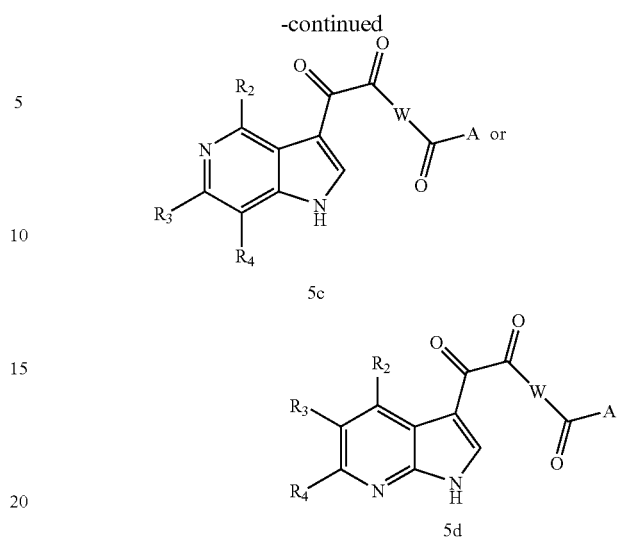

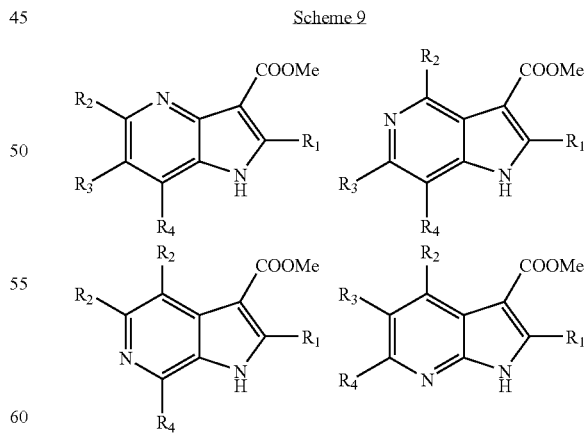

Scheme 8 shows the synthesis of 4-azaindole derivatives 1b-5b, 5-azaindole derivatives 1c-5c, and 7-azaindole derivatives 1d-5d. The methods used to synthesize 1b-5b, 1c-5c, and 1d-5d are the same methods described for the synthesis of 1a-5a as described in Scheme 3. It is understood, for the purposes of Scheme 8, that 1b is used to synthesize 2b-5b, 1c provides 2c-5c and 1d provides 2d-5d.

The compounds where there is a single carbonyl between the azaindole and group W can be prepared by the method of Kelarev, V. I.; Gasanov, S. Sh.; Karakhanov, R. A.; Polivin, Yu. N.; Kuatbekova, K. P.; Panina, M. E.; *Zh. Org. Khim* 1992, 28(12), 2561-2568. In this method azaindoles are reacted with trichloroacetyl chloride in pyridine and then subsequently with KOH in methanol to provide the 3-carbomethoxy azaindoles shown in Scheme 4 which can then be hydrolyzed to the acid and carried through the coupling sequence with HW(C=O)A to provide the compounds of Formula I wherein a single carbonyl links the azaindole moiety and group W.

Scheme 9

An alternative method for carrying out the sequence outlined in steps B-D (shown in Scheme 8) involves treating an azaindole, such as 11, obtained by procedures described in the literature or from commercial sources, with MeMgI and ZnCl$_2$, followed by the addition of ClCOCOCl (oxalyl chloride) in either THF or Et$_2$O to afford a mixture of a glyoxyl chloride azaindole, 12a, and an acyl chloride azaindole, 12b. The resulting mixture of glyoxyl chloride azaindole and acyl chloride azaindole is then coupled with mono-benzoylated piperazine derivatives under basic conditions to afford the products of step D as a mixture of compounds, 13a and 13b, where either one or two carbonyl groups link the azaindole and group W. Separation via chromatographic methods which are well known in the art provides the pure 13a and 13b. This sequence is summarized in Scheme 10, below.

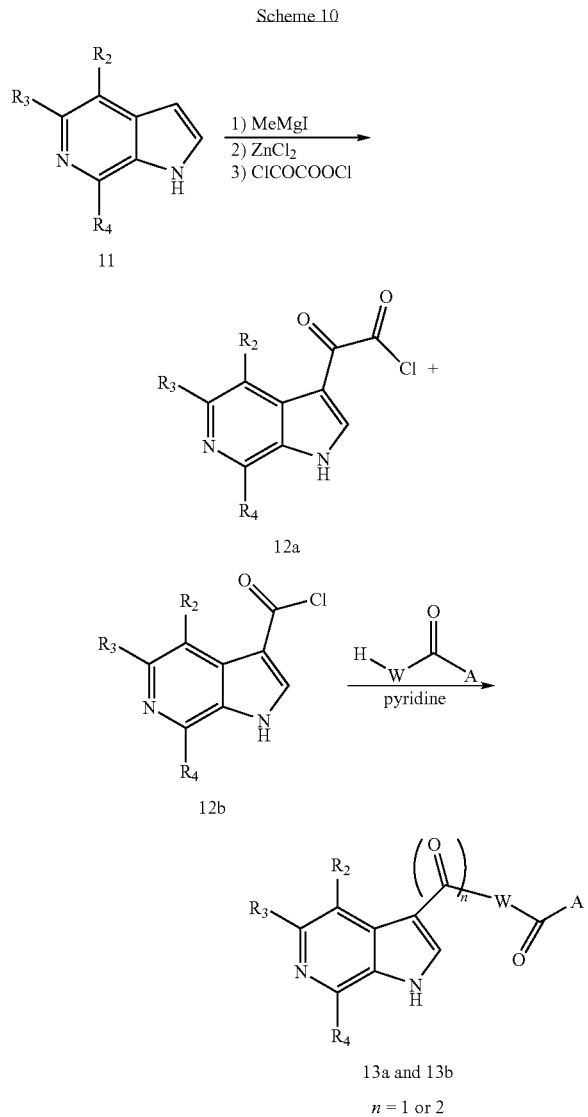

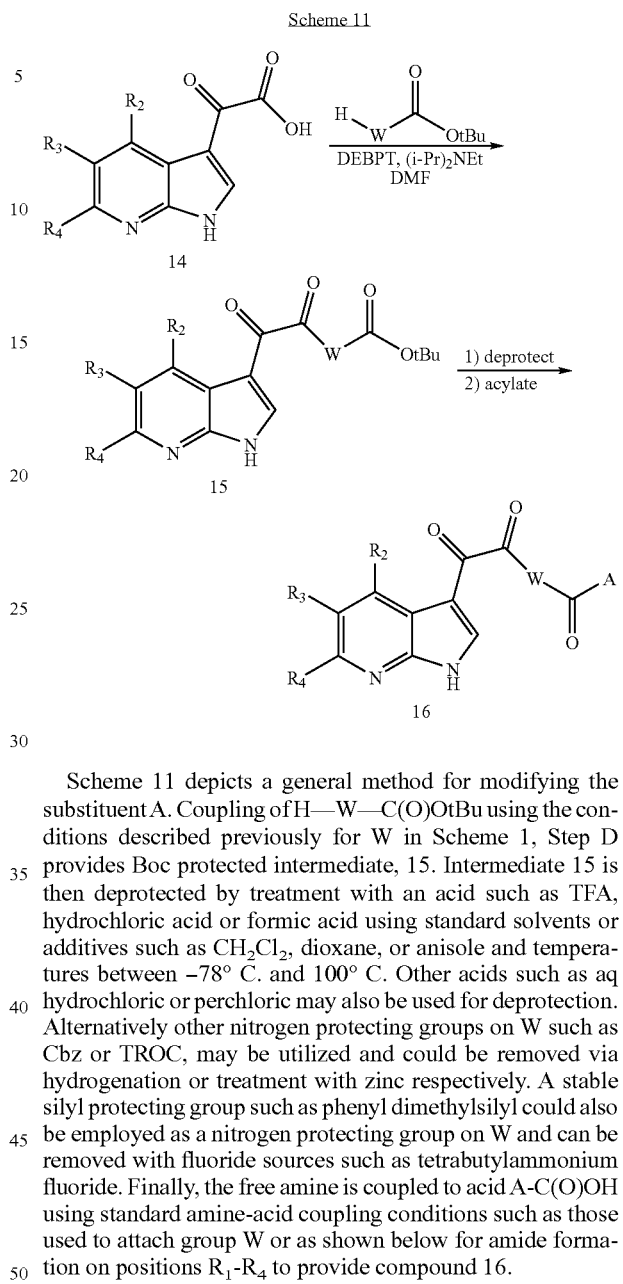

Scheme 11 depicts a general method for modifying the substituent A. Coupling of H—W—C(O)OtBu using the conditions described previously for W in Scheme 1, Step D provides Boc protected intermediate, 15. Intermediate 15 is then deprotected by treatment with an acid such as TFA, hydrochloric acid or formic acid using standard solvents or additives such as CH$_2$Cl$_2$, dioxane, or anisole and temperatures between −78° C. and 100° C. Other acids such as aq hydrochloric or perchloric may also be used for deprotection. Alternatively other nitrogen protecting groups on W such as Cbz or TROC, may be utilized and could be removed via hydrogenation or treatment with zinc respectively. A stable silyl protecting group such as phenyl dimethylsilyl could also be employed as a nitrogen protecting group on W and can be removed with fluoride sources such as tetrabutylammonium fluoride. Finally, the free amine is coupled to acid A-C(O)OH using standard amine-acid coupling conditions such as those used to attach group W or as shown below for amide formation on positions R$_1$-R$_4$ to provide compound 16.

Scheme 12 a preferred method for preparing HW—C(O)-A. Specific details are contained in the experimental section. Additional examples of the preparation of 3-amino and 3-aminomethyl pyrrolidines are described in Patane et al PCT Patent Application WO 98/57640. Scheme 13 depicts a specific route to compounds of the invention Q in which Q is an indole with a dicarbonyl at the 3 position and W is an aminomethyl pyrollidine attached to Q via the primary amine. A specific procedure where A is phenyl is contained in the experimental. Q could also be alternative indoles and azaindoles and A other substituents as needed to prepare compounds of the invention. Scheme 14 describes a similar sequence except that the amino methyl pyrrolidine, W is attached to the dicarbonyl via the secondary ring nitrogen and A is —OtBu. As shown, acidic removal of the tertbutoxycarbonyl group provides a free primary amine or amine hydrochloride which may be reacted with acyl chlorides or chloroformates to give additional compounds of the invention with various A groups. The example where A is phenyl is described in detail in the experimental section. Scheme 15 describes similar chemistry but shows how the 7-position of the indole may be functionalized by an aldehyde, carboxylic acid, or methyl carboxamide. This sequence is also described in the experimental section. A chemist skilled in the art can recognize how this chemistry could be utilized on other examples where Q, W, and A are modified.

Scheme 12

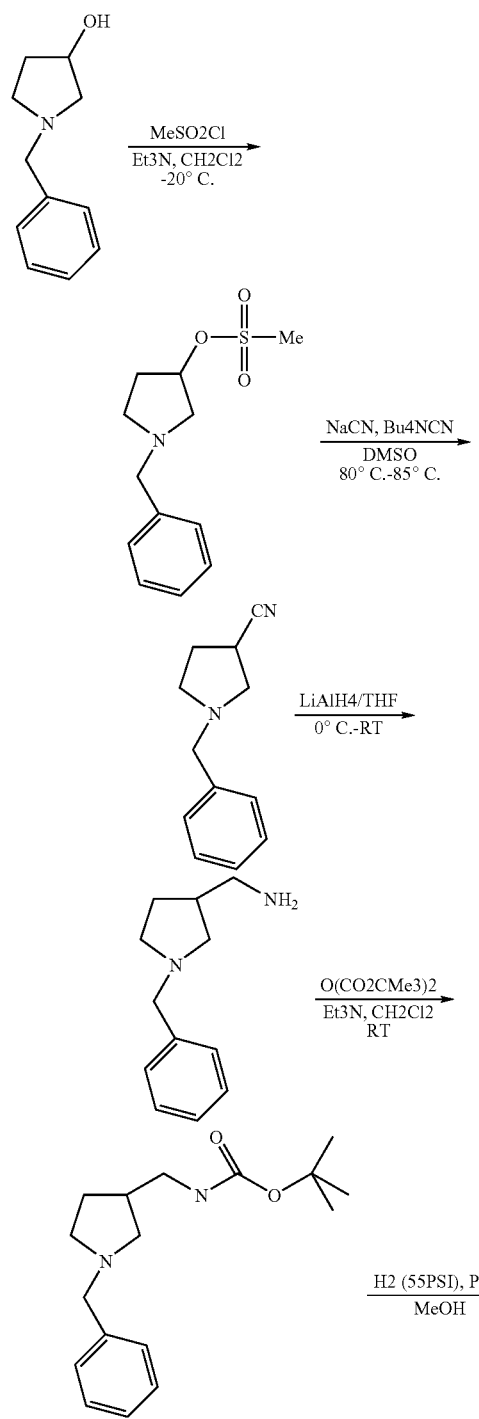

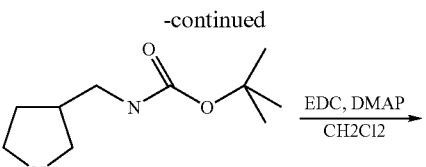

-continued

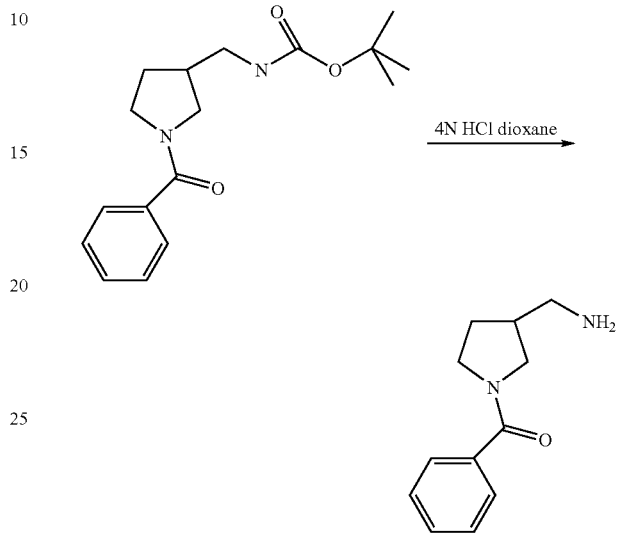

Scheme 13

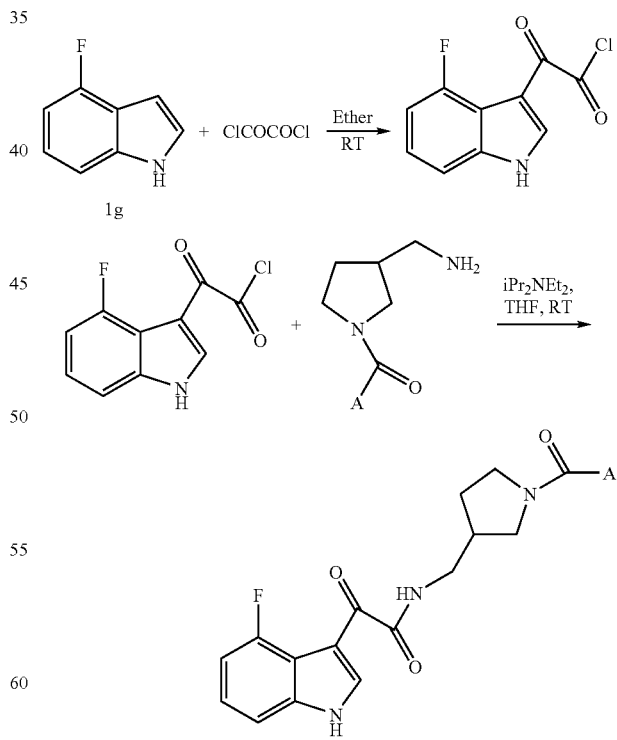

A = -Ph in one exemplified case

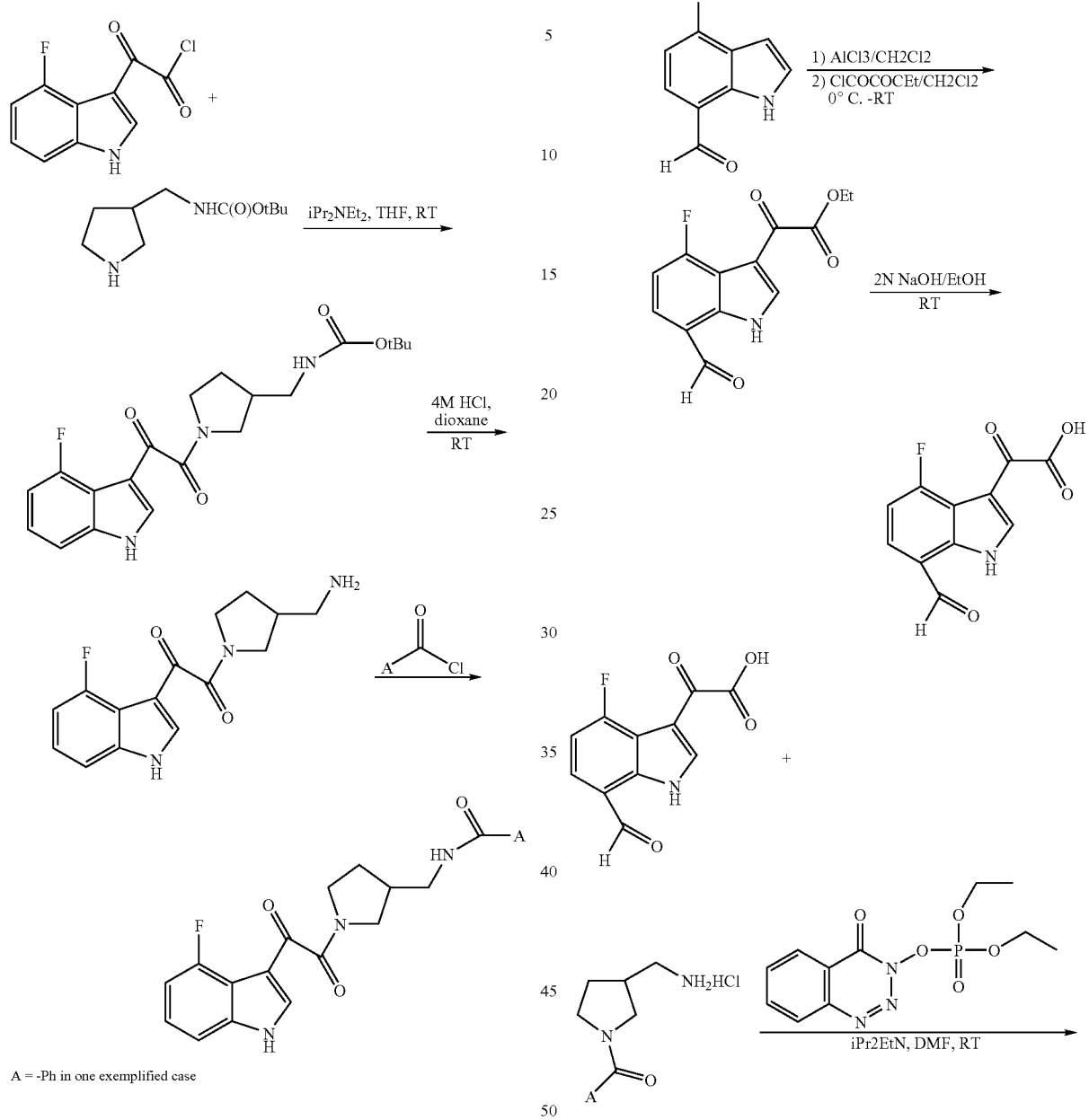
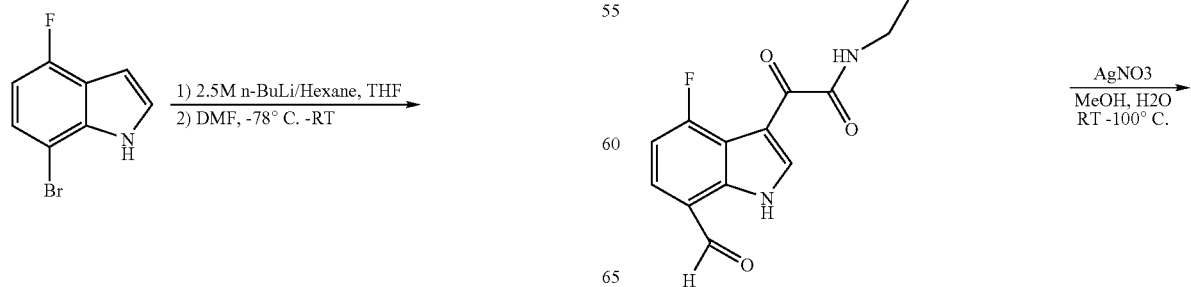

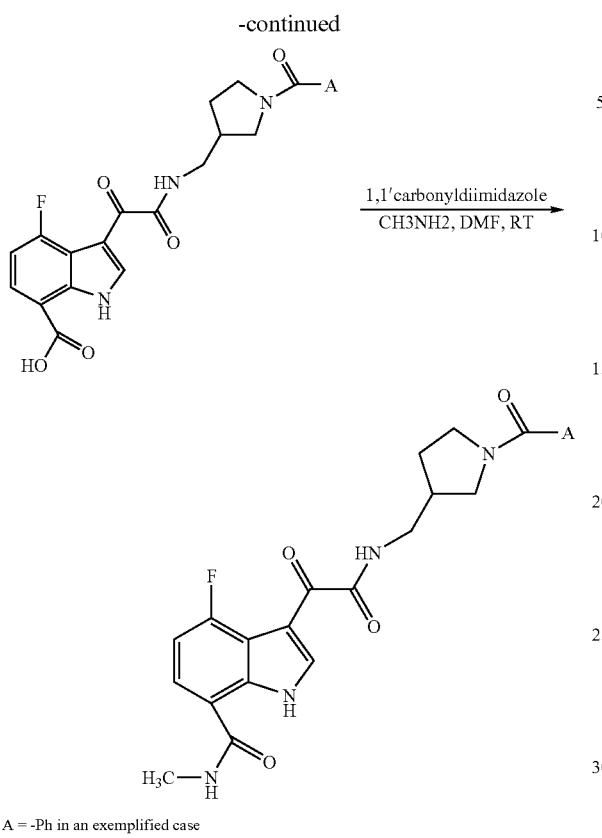

A = -Ph in an exemplified case

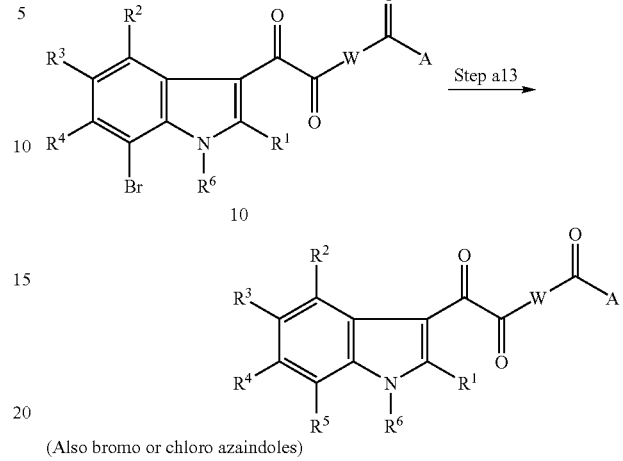

(Also bromo or chloro azaindoles)

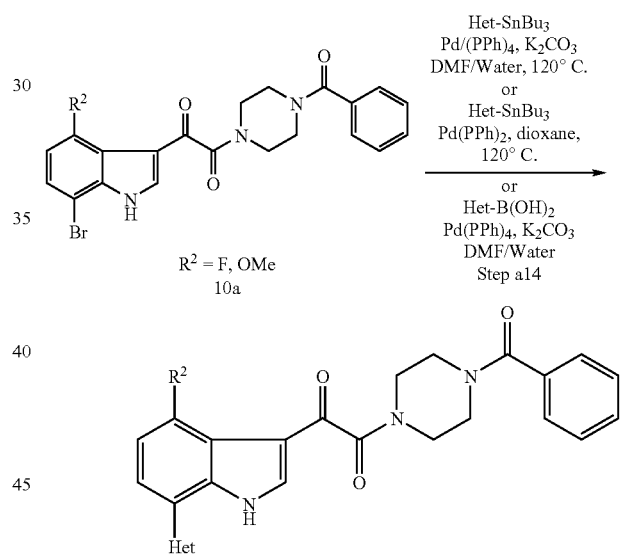

As shown below in Scheme 16, step a13, suitable substituted indoles, such as the bromoindole intermediate, 10, may undergo metal mediated couplings with aryl groups, heterocycles, or vinyl stannanes to provide compounds within Formula I wherein $R^5$ is aryl, heteroaryl, or heteroalicyclic for example. The bromoindole intermediates, 10 (or indole triflates or iodides) may undergo Stille-type coupling with heteroarylstannanes as shown in Scheme 17, step a14. Conditions for this reaction are well known in the art and references 72-74 as well as reference 91 provide numerous conditions in addition to the specific examples provided in Scheme 17 and in the specific embodiments. It can be well recognized that an indole stannane could also couple to a heterocyclic or aryl halide or triflate to construct compounds of Formula I. Suzuki coupling (reference 71) between the bromo intermediate, 10, and a suitable boronate could also be employed and some specific examples are contained in this application. Other Suzuki conditions, partners, and leaving groups have utility. Suzuki couplings between chloro intermediates are also feasible. If standard conditions fail new specialized catalysts and conditions can be employed. Procedures describing catalysts which are useful for coupling boronates with aryl and heteroaryl chlorides are known in the art (reference 100 a-g). The boronate could also be formed on the indole and then subjected to Suzuki coupling conditions. The same coupling methodologies may be used in the case where Q contains azaindoles rather than indoles.

Chemistry

All Liquid Chromatography (LC) data were recorded on a Shimadzu LC-10AS liquid chromatograph using a SPD-10AV UV-Vis detector with Mass Spectrometry (MS) data determined using a Micromass Platform for LC in electrospray mode.

LC/MS Method (i.e., compound identification)

Note: column A is used unless otherwise indicated in the preparation of intermediates or examples.

Column A: YMC ODS-A S7 3.0×50 mm column

Column B: PHX-LUNA C18 4.6×30 mm column

Column C: XTERRA ms C18 4.6×30 mm column

Column D: YMC ODS-A C18 4.6×30 mm column

Column E: YMC ODS-A C18 4.6×33 mm column

Column F: YMC C18 S5 4.6×50 mm column

Column G: XTERRA C18 S7 3.0×50 mm column

Gradient: 100% Solvent A/0% Solvent B to 0% Solvent A/100% Solvent R, in min.

Gradient time: 2 minutes

Hold time 1 minute

Flow rate: 5 mL/min

Detector Wavelength: 220 nm

Solvent A: 10% MeOH/90% H$_2$O/0.1% Trifluoroacetic Acid

Solvent B: 10% H$_2$O/90% MeOH/0.1% Trifluoroacetic Acid

Compounds purified by preparative HPLC were diluted in MeOH (1.2 mL) and purified using the following methods on a Shimadzu LC-10A automated preparative HPLC system or on a Shimadzu LC-8A automated preparative HPLC system with detector (SPD-10AV UV-VIS) wavelength and solvent systems (A and B) the same as above.

Preparative HPLC Method (i.e., Compound Purification)

Purification Method Initial gradient (40% B, 60% A) ramp to final gradient (100% B, 0% A) over 20 minutes, hold for 3 minutes (100% B, 0% A)

Solvent A: 10% MeOH/90% H$_2$O/0.1% Trifluoroacetic Acid

Solvent B: 10% H$_2$O/90% MeOH/0.1% Trifluoroacetic Acid

Column: YMC C18 S5 20×100 mm column

Detector Wavelength: 220 nm

Intermediate 1

Methanesulfonic acid 1-benzyl-pyrrolidin-3-ylmethyl ester

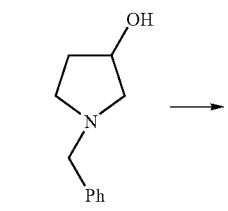
1-Benzyl-pyrrolidin-3-ol

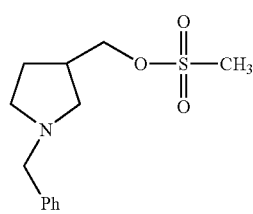
Methanesulfonic acid 1-benzyl-pyrrolidin-3-ylmethyl ester

This transformation was carried out via the method in J. L. Marco et. al. reference 96. Methanesulfonyl chloride (0.10 mol, 7.8 mL) was added slowly to a solution of racemic 1-benzyl-pyrrolidin-3-ol (0.085 mol, 15 g) in 150 mL of dichloromethane which was stirring under a nitrogen atmosphere at a temperature of −20° C. The reaction was stirred for an additional 1.5 h after addition was completed. The reaction was poured into a separatory funnel containing additional dichloromethane and washed with five thirty mL portions of saturated aqueous sodium bicarbonate. The organic layer was washed with one portion of water and then one portion of saturated aq NaCl. The organic layer was dried over anhydrous sodium sulfate, filtered, and concentrated in vacuo to provide 22.75 g of crude mesylate which was used directly following characterization by proton NMR and LC/MS.

Intermediate 2

1-Benzyl-pyrrolidine-3-carbonitrile

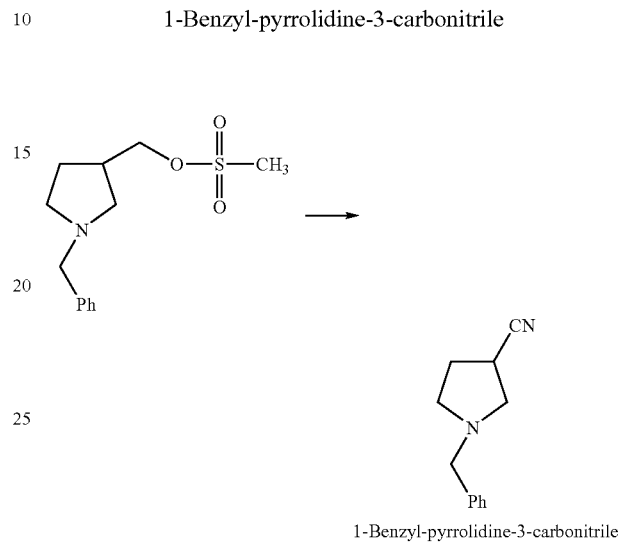
1-Benzyl-pyrrolidine-3-carbonitrile

This transformation was carried out using the method described in C. Thomas et. al. reference 97. The mesylate of racemic 1-benzyl-pyrrolidin-3-ol (0.039 mol, 10 g), prepared as described above, sodium cyanide (0.24 mol, 15 g) and tetrabutylammonium cyanide (10 g, 0.037 mol) in 75 mL of DMSO was stirred at 80-85° C. for 16 h. The reaction mixture was partitioned between diethyl ether and sat. aq sodium bicarbonate. The aqueous layer was extracted twice with ether and the combined organic layer was washed successively with sodium bicarbonate, water, and sat aq. NaCl. The organic layer was dried over anhydrous magnesium sulfate, concentrated, and purified by flash chromatography over silica gel using a gradient of 20 to 30% ethyl acetate in hexane to afford 5.5 g of the desired product.

Intermediate 3

C-(1-Benzyl-pyrrolidin-3-yl)-methylamine

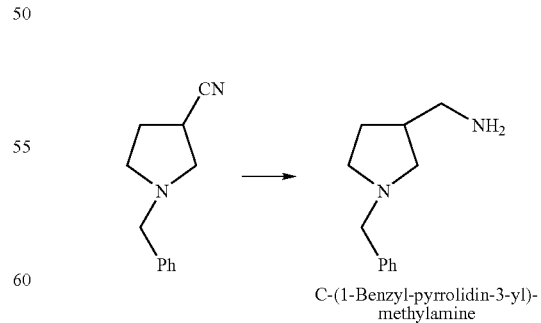
C-(1-Benzyl-pyrrolidin-3-yl)-methylamine

This reaction was carried out according to the procedure in M. R. Pavia et. al. reference 98. The nitrile (0.03 mol, 5.5 g) was dissolved in THF and cooled to 0° C. Lithium aluminum hydride (0.03 mol, 1.14 g) was added into the solution in one portion. After the addition was finished, the colling bath was removed and the reaction was stirred at ambient temperature for 18 h. The reaction was filtered and the filtrate was a concentrated in vacuo to provide the crude product which was used directly in the next reaction.

Intermediate 4

(1-Benzyl-pyrrolidin-3-ylmethyl)-carbamic acid tert-butyl ester

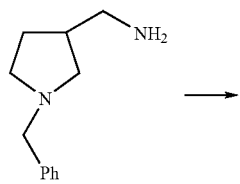
C-(1-Benzyl-pyrrolidin-3-yl)-methylamine

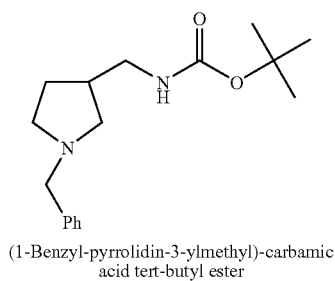
(1-Benzyl-pyrrolidin-3-ylmethyl)-carbamic acid tert-butyl ester

A mixture of crude amine (0.028 mol, 5.3 g), triethylamine (0.034 mol, 4.7 mL), and ditertbutyl dicarbonate (0.034 mol, 7.4 g) in dichloromethane was stirred at ambient temperature for 3 h. The reaction was diluted with dichloromethane, and then washed with water and then sat aq NaCl. The organic extract was dried over anhydrous magnesium sulfate, filtered, and concentrated in vacuo. Purification via flash chromatography over silica gel provided 4.2 g of the desired carbamate. 1H NMR (300 MHz, CDCl$_3$): 7.32~7.30 (m, 5H), 3.59~3.58 (m, 2H), 3.17~3.02 (m, 2H), 2.73~2.28 (m, 5H), 2.04~1.90 (m, 1H), 1.60~1.48 (m, 1H), 1.45 (s, 9H).

Intermediate 5

Pyrrolidin-3-ylmethyl-carbamic acid tert-butyl ester

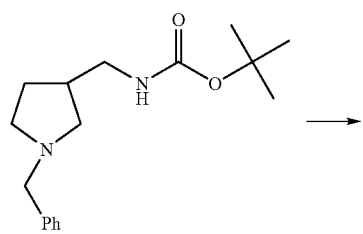
(1-Benzyl-pyrrolidin-3-ylmethyl)-carbamic acid tert-butyl ester

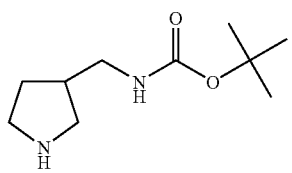
Pyrrolidin-3-ylmethyl-carbamic acid tert-butyl ester

The benzyl amine (4.2 g) and 2.1 g of 10% Pd/C in methanol was shaken under 50PSI of hydrogen on a Parr apparatus for 20 h. The reaction mixture was filtered through celite and concentrated in vacuo to give a residue which was used directly without further purification. 1H NMR (300 MHz, CDCl$_3$): 3.15~1.82 (m, 8H), 1.55~1.45 (m, 1H), 1.43 (s, 9H).

Intermediate 6

(1-Benzoyl-pyrrolidin-3-ylmethyl)-carbamic acid tert-butyl ester

Pyrrolidin-3-ylmethyl-carbamic acid tert-butyl ester

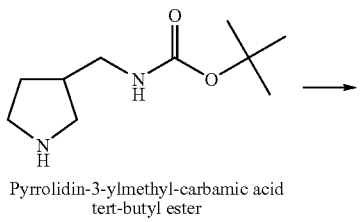
(1-Benzoyl-pyrrolidin-3-ylmethyl)-carbamic acid tert-butyl ester

The amine (14.65 mmol, 2.93 g) was dissolved in dichloromethane and treated with DMAP (14.65 mmol, 1.79 g), EDC (14.65 mmol, 2.80 g), and then benzoic acid (13.18 mmol, 0.9 eq). The reaction was stirred for 16 h at ambient temperature and then diluted with dichloromethane. The organic layer was washed with water and sat aq. NaCl and dried over anhydrous sodium sulfate. The solution was filtered and concentrated in vacuo to provide a residue which was purified by flash chromatography over silica gel to provide 3.06 g of the desired benzamide. ¹H NMR (300 MHz, CDCl₃): 7.55~7.34 (m, 5H), 3.80~3.10 (m, 6H), 2.55~1.58 (m, 3H), 1.40 (s, 9H).

Intermediate 7

(3-Aminomethyl-pyrrolidin-1-yl)-phenyl-methanone

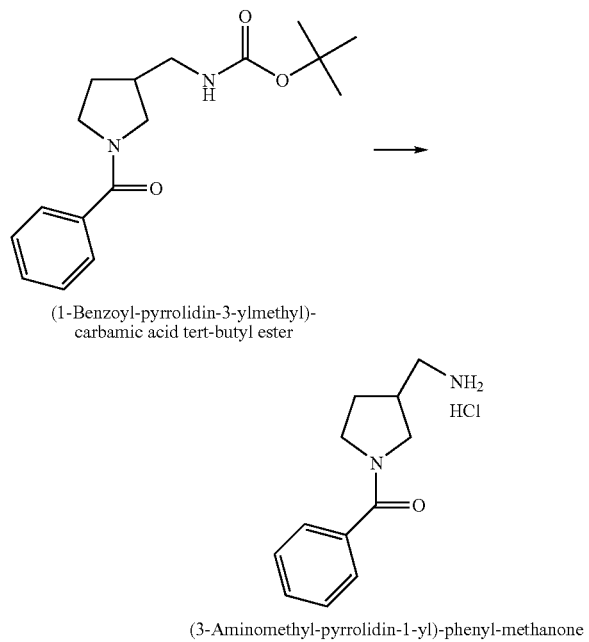

(1-Benzoyl-pyrrolidin-3-ylmethyl)-carbamic acid tert-butyl ester

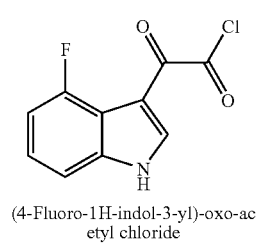

(3-Aminomethyl-pyrrolidin-1-yl)-phenyl-methanone

The carbamate was stirred in 20 mL of 4N HCl in dioxane for 20 h. The reaction mixture was concentrated on a rotary evaporator and dried under vacuum to provide the hydrochloride salt which was used directly without further purification.

Example 1

N-(1-Benzoyl-pyrrolidin-3-ylmethyl)-2-(4-fluoro-1H-indol-3-yl)-2-oxo-acetamide

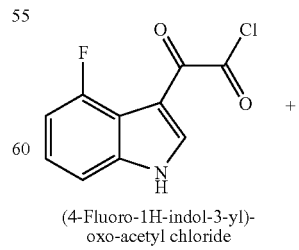

(4-Fluoro-1H-indol-3-yl)-oxo-acetyl chloride

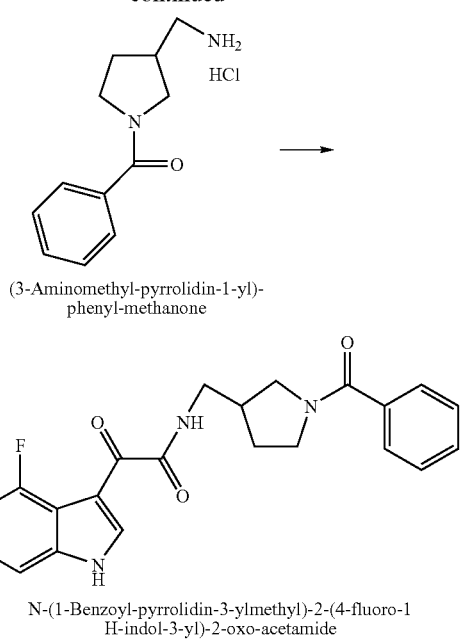

(3-Aminomethyl-pyrrolidin-1-yl)-phenyl-methanone

N-(1-Benzoyl-pyrrolidin-3-ylmethyl)-2-(4-fluoro-1H-indol-3-yl)-2-oxo-acetamide

The acid chloride (1 mmol, 225 mg) was added to a solution of the amine hydrochloride (1 mmol, 240 mg) and diisopropyl ethyl amine (10 mmol, 1.74 mL) in 5 mL of anhydrous THF under a nitrogen atmosphere. The reaction was stirred for 16 h at ambient temperature and then poured into ethyl acetate. The organic layer was washed with water and then sat aq NaCl and then dried over anhydrous magnesium sulfate. Filtration and concentration in vacuo provided a crude product which was purified by flash chromatography over silica gel to provide 208 mg of the desired N-(1-Benzoyl-pyrrolidin-3-ylmethyl)-2-(4-fluoro-1H-indol-3-yl)-2-oxo-acetamide.

1H NMR (500 MHz, CD3OD): 8.69 (s), 8.56 (s), 1H. 7.55~7.40 (m, 5H), 7.31~7.20 (m, 2H), 6.96~6.87 (m, 1H), 3.81~3.29 (m, 6H), 2.70~1.73 (m, 3H).

LC/MS: (ES+) m/z (M+H)+=394, RT=1.06.

Example 2

{1-[2-(4-Fluoro-1H-indol-3-yl)-2-oxo-acetyl]-pyrrolidin-3-ylmethyl}-carbamic acid tert-butyl ester

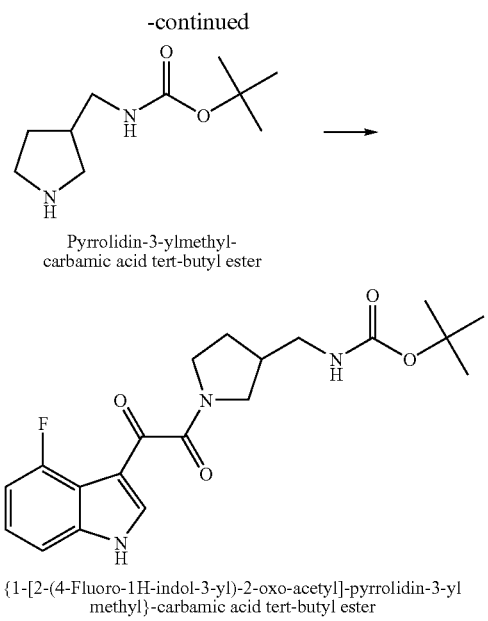

Pyrrolidin-3-ylmethyl-
carbamic acid tert-butyl ester

{1-[2-(4-Fluoro-1H-indol-3-yl)-2-oxo-acetyl]-pyrrolidin-3-yl
methyl}-carbamic acid tert-butyl ester The acid chloride (2 mmol, 453 mg) was added to a solution of the amine hydrochloride (2 mmol, 400 mg) and diisopropyl ethyl amine (4 mmol, 0.7 mL) in 12 mL of anhydrous THF under a nitrogen atmosphere. The reaction was stirred for 18 h at ambient temperature and then poured into ethyl acetate. The organic layer was washed with water and then sat aq NaCl and then dried over anhydrous magnesium sulfate. Filtration and concentration in vacuo provided a crude product which was purified by flash chromatography over silica gel to provide 475 mg of the desired 3-{[2-(4-Fluoro-1H-indol-3-yl)-2-oxo-acetylamino]-methyl}-pyrrolidine-1-carboxylic acid tert-butyl ester.

1H NMR (500 MHz, CD3OD): 8.17 (s), 8.14 (S), 1H. 7.32~7.24 (m, 2H), 6.97~6.93 (m, 1H), 3.73~3.04 (m, 6H), 2.46~2.43 (m, 1H), 2.09~2.01 (m, 1H), 1.74~1.73 (m, 1H), 1.44 (s, 9H).

Intermediate 8

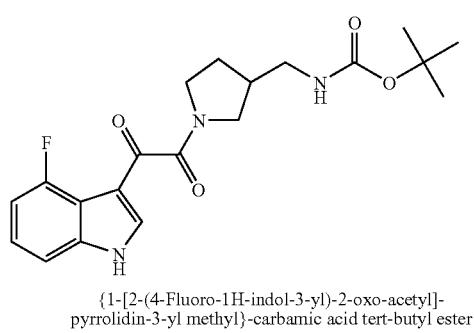

{1-[2-(4-Fluoro-1H-indol-3-yl)-2-oxo-acetyl]-
pyrrolidin-3-yl methyl}-carbamic acid tert-butyl ester

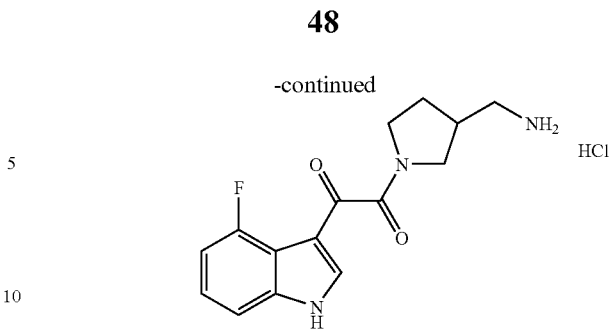

The carbamate was stirred in 15 mL of 4N HCl in dioxane for 20 h. The reaction mixture was concentrated on a rotary evaporator and dried under vacuum to provide the hydrochloride salt which was used directly without further purification.

Example 3

N-{1-[2-(4-Fluoro-1H-indol-3-yl)-2-oxo-acetyl]-
pyrrolidin-3-ylmethyl}-benzamide and Example
4N-{1-[2-(1-Benzoyl-4-fluoro-1H-indol-3-yl)-2-
oxo-acetyl]-pyrrolidin-3-ylmethyl}-benzamide

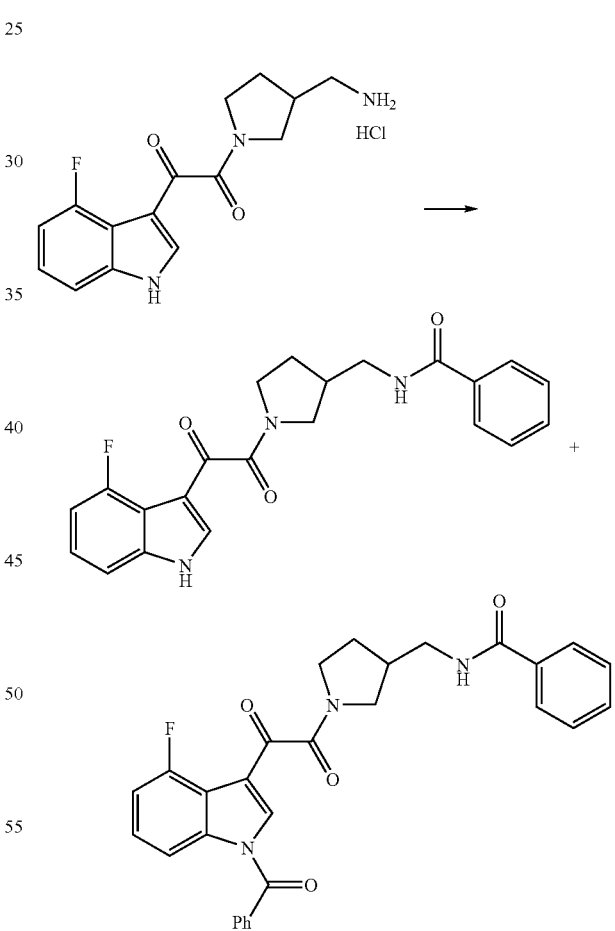

Benzoyl chloride (0.46 mmol, 54 µL) and then diisopropyl ethyl amine (0.92 mmol, 0.16 mL) were added to a stirring solution of amine hydrochloride (0.46 mmol, 150 mg) in 5 mL of THF under an atmosphere of nitrogen at ambient temperature. The reaction was stirred for 18 h and then the THF was removed in vacuo. The residue was dissolved in ethyl acetate and washed with water and then sat aq NaCl. The organic extract was dried, filtered, concentrated, and purified via flash chromatography to the desired product of example 3:

1H NMR (500 MHz, CD3OD): 8.18 (s), 8.14 (s), 1H. 7.85~7.82 (m, 1H), 7.72~7.68 (m, 1H), 7.54~7.24 (m, 5H), 6.97~6.90 (m, 1H), 3.80~3.29 (m, 6H), 2.67~2.61 (m, 1H), 2.20~2.05 (m, 1H), 1.87~1.81 (m, 1H).

LC/MS: (ES+) m/z (M+H)+=394, RT=1.74.

and the bis benzylated product Example 4 which resulted from a second benzylation of the indole nitrogen:

LC/MS: (ES+) m/z (m+H)+=498; RT=1.46

Example 5

N-(1-Benzoyl-pyrrolidin-3-ylmethyl)-2-(4-fluoro-7-formyl-1H-indol-3-yl)-2-oxo-acetamide

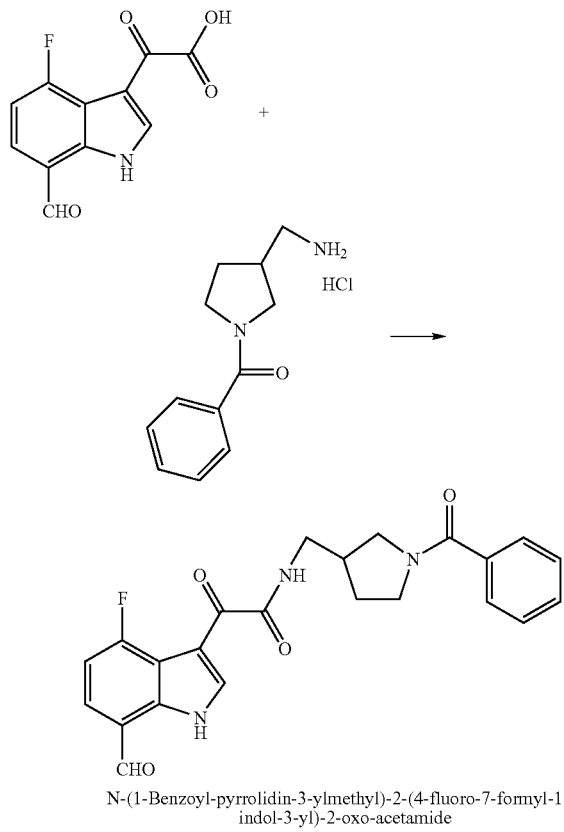

N-(1-Benzoyl-pyrrolidin-3-ylmethyl)-2-(4-fluoro-7-formyl-1H-indol-3-yl)-2-oxo-acetamide DEPBT (2.13 mmol, 514 mg) was added to a stirring solution of the aldehyde acid (prepared as described in WO 00/76521, 2.13 mmol, 500 mg), amine hydrochloride (2.13 mmol, 514 mg), and diisopropyl ethylamine (4.26 mmol, 0.74 mL) in 5 mL of DMF at ambient temperature. The reaction was stirred for 16 h and then the DMF was removed in vacuo. The residue was dissolved in ethyl acetate and water was added. After separation the water layer was reextracted with ethyl acetate. The combined organic extracts were dried over anhydrous magnesium sulfate, concentrated and chromatographed over silica gel to provide the desired product.

1H NMR (300 MHz, CD3OD): 10.06 (s, 1H); 8.79 (s), 8.72 (s), 1H, 7.89~7.84 (m, 1H); 7.53~7.40 (m, 5H); 7.15~7.06 (m, 1H); 3.81~3.29 (m, 6H); 2.68~2.51 (m, 1H); 2.17~2.00 (m, 1H); 1.87~1.72 (m, 1H).

LC/MS: (ES+) m/z (m+H)+=422; RT=1.29.

Example 6

N-(1-Benzoyl-pyrrolidin-3-ylmethyl)-2-oxo-2-(1H-pyrrolo[2,3-b]pyridin-3-yl)-acetamide

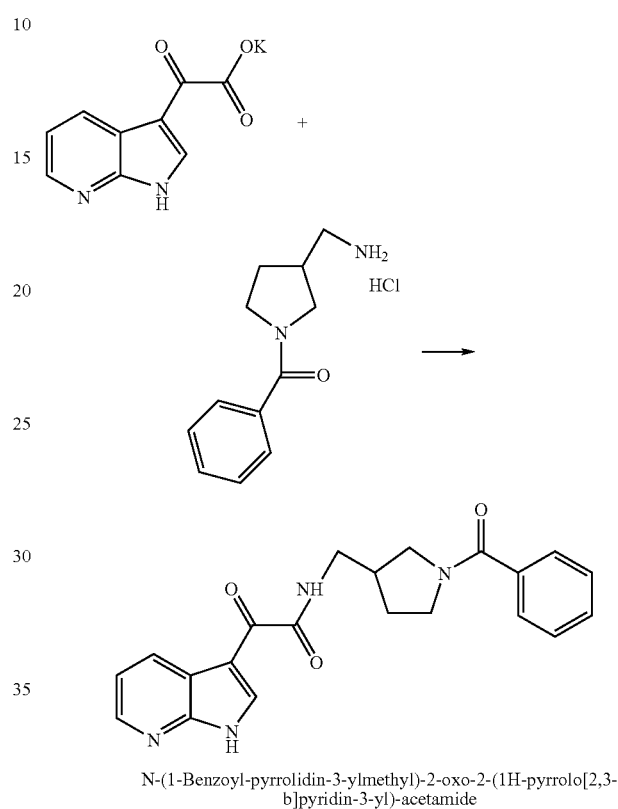

N-(1-Benzoyl-pyrrolidin-3-ylmethyl)-2-oxo-2-(1H-pyrrolo[2,3-b]pyridin-3-yl)-acetamide DEPBT (1.32 mmol, 395 mg) was added to a stirring solution of the potassium salt (prepared as described in WO 01/62255, 1.32 mmol, 300 mg), amine hydrochloride (1.32 mmol, 318 mg), and diisopropyl ethylamine (2.64 mmol, 0.46 mL) in 3 mL of DMF at ambient temperature. The reaction was stirred for 16 h and then the DMF was removed in vacuo. The residue was dissolved in ethyl acetate and water was added. After separation the water layer was reextracted with ethyl acetate. The combined organic extracts were washed with sat aq NaCl, dried over anhydrous magnesium sulfate, concentrated and chromatographed over silica gel to provide 268 mg of the desired product.

1H NMR (500 MHz, CD3OD): 8.92~8.89 (m), 8.81~8.79 (m), 1H, 8.68~8.60 (m, 1H); 8.34~8.8.32 (m, 1H); 7.54~7.43 (m, 5H); 7.33~7.7.26 (m, 1H); 3.96~3.26 (m, 6H); 2.66~2.52 (m, 1H); 2.16~2.05 (m, 1H); 1.85~1.74 (m, 1H).

LC/MS: (ES+) m/z (m+H)+=377; RT=1.18

Example 7

3-(1-Benzoyl-pyrrolidin-3-ylmethyl)-aminooxalyl)-4-fluoro-1H-indole-7-carboxylic acid

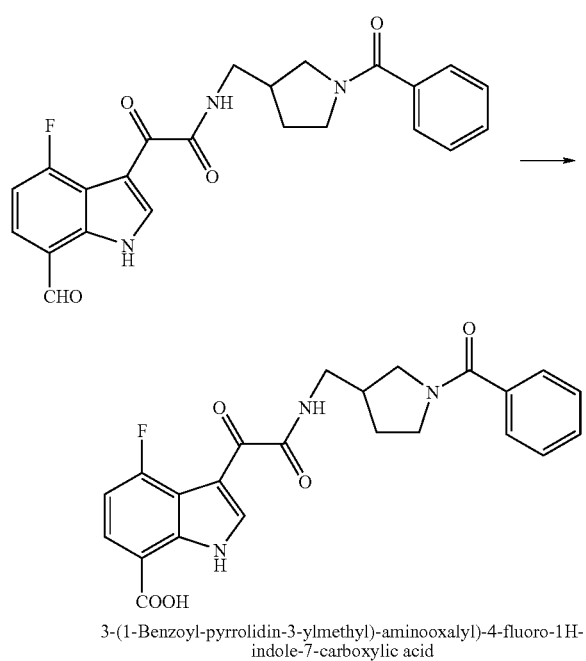

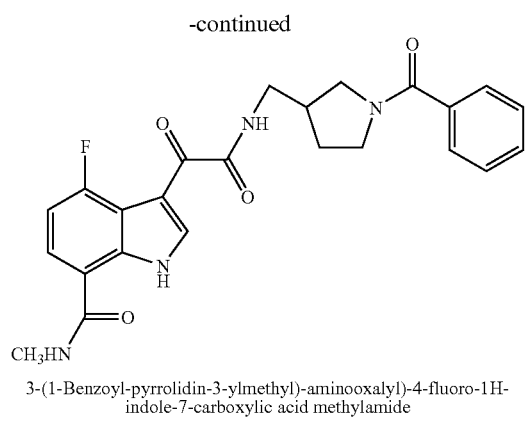

3-(1-Benzoyl-pyrrolidin-3-ylmethyl)-aminooxalyl)-4-fluoro-1H-indole-7-carboxylic acid methylamide The acid (19 mg, 1 equivalent) was dissolved in 1 mL of DMF and 1.5 equivalents of 1,1-carbonyl diimidazole was added. The reaction was stirred at ambient temperature for 15 min and then 4 equivalents (0.1 ml) of 2N methyl amine in THF was added. The reaction was stirred overnight and then the DMF was removed in vacuo. The residue was chromatographed to afford 12 mg of the desired methyl amide.

LC/MS: (ES+) m/z (m+H)+=451; RT=1.26

Example 9

N-{1-[2-(7-Bromo-4-fluoro-1H-indol-3-yl)-2-oxo-acetyl]-pyrrolidin-3-ylmethyl}-benzamide 3-(1-Benzoyl-pyrrolidin-3-ylmethyl)-aminooxalyl)-4-fluoro-1H-indole-7-carboxylic acid Silver nitrate (AgNO3, 1.48 mmol, 252 mg) was dissolved in 2 mL of water. A solution of NaOH (2.96 mmol, 118 mg) in 2 mL of methanol and 2 mL of water was added to the silver nitrate solution and a brown precipitate formed. The aldehyde (0.74 mmol, 313 mg) was added into the solution/precipitate in one portion. The reaction was heated to 90° C. and stirred for 15 h. After colling to ambient temperature, the reaction was filtered through celite using ethyl acetate washes. The filtrate was extracted with ethyl acetate. The aqueous layer was acidified with 2N HCl to about PH 2. The resulting solid was collected by filtration to give the desired acid. 1H NMR (500 MHz, CD3OD): 8.79 (s), 8.70 (s), 1H, 8.05~7.92 (m, 1H); 7.53~7.44 (m, 5H); 7.05~6.93 (m, 1H); 3.78~3.26 (m, 6H); 2.66~2.53 (m, 1H); 2.17~2.06 (m, 1H); 1.84~1.75 (m, 1H).

LC/MS: (ES+) m/z (m+H)+=438; RT=1.33.

Example 8

3-(1-Benzoyl-pyrrolidin-3-ylmethyl)-aminooxalyl)-4-fluoro-1H-indole-7-carboxylic acid methylamide

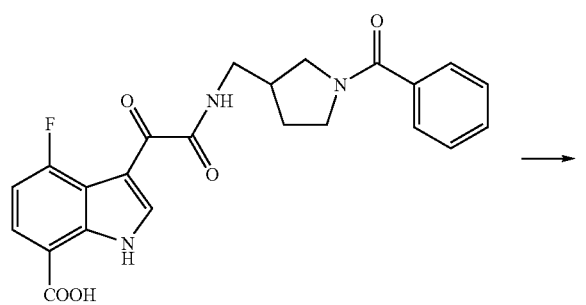

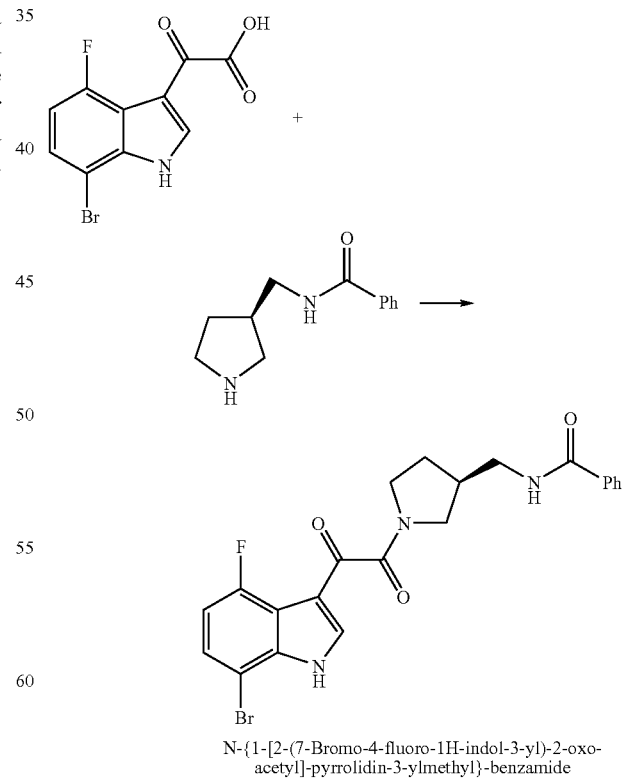

N-{1-[2-(7-Bromo-4-fluoro-1H-indol-3-yl)-2-oxo-acetyl]-pyrrolidin-3-ylmethyl}-benzamide The ketoacid (0.97 mmol, 280 mg), the amine (0.97 mmol, 200 mg) and diisopropyl ethyl amine (0.34 mL) and DEPBT (0.97 mmol, 292 mg) were dissolved in 2 mL of dry DMF under an atmosphere of nitrogen. The reaction was stirred for 36 h at ambient temperature and then poured into 10 mL of ethyl acetate. The organic layer was washed with two 10 mL portions of water and then the aqueous layer was back extracted with 10 mL of EtOAc. The combined organic extracts were dried over anhydrous magnesium sulfate. Filtration and concentration in vacuo provided a crude product which was purified by flash chromatography over silica gel using gradients of 50 to 100% EtOAc:Hexane then 2 to 5% MeOH/EtOAc to provide 29 mg of the desired amide as a light brown solid.

1H NMR (500 MHz, CD3OD): 8.43 (s), 8.38 (s), 1H, 8.01~7.97 (m, 1H); 7.83~7.79 (m, 1H); 7.69~7.34 (m, 4H); 4.13~1.20 (m, 9H).

LC/MS: (ES+) m/z (m+H)+=475; RT=1.27.

Example 10

N-{1-[2-(7-Bromo-4-fluoro-1H-indol-3-yl)-2-oxo-acetyl]-pyrrolidin-3-ylmethyl}-benzamide

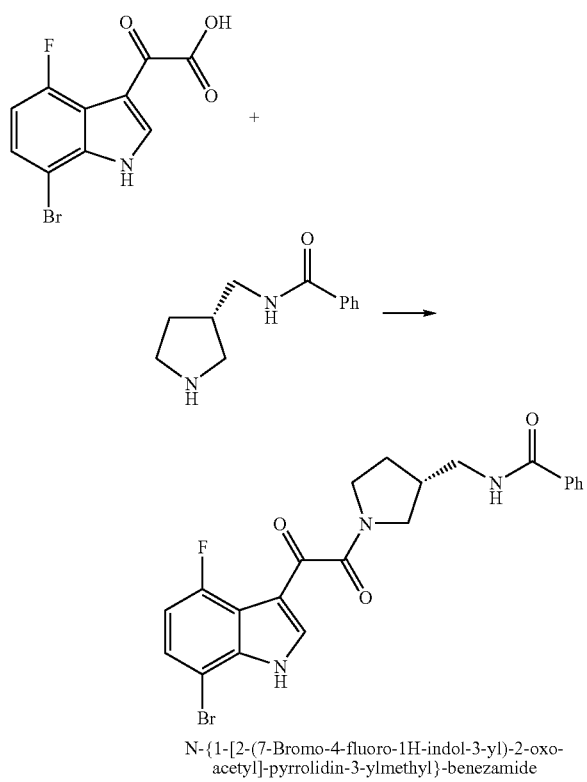

N-{1-[2-(7-Bromo-4-fluoro-1H-indol-3-yl)-2-oxo-acetyl]-pyrrolidin-3-ylmethyl}-benezamide The ketoacid (0.97 mmol, 280 mg), the amine (0.97 mmol, 200 mg) and diisopropyl ethyl amine (0.34 mL) and DEPBT (0.97 mmol, 292 mg) were dissolved in 2 mL of dry DMF under an atmosphere of nitrogen. The reaction was stirred for 36 h at ambient temperature and then poured into 10 mL of ethyl acetate. The organic layer was washed with two 10 mL portions of water and then the aqueous layer was back extracted with 10 mL of EtOAc. The combined organic extracts were dried over anhydrous magnesium sulfate. Filtration and concentration in vacuo provided a crude product which was purified by flash chromatography over silica gel using gradients of 50 to 100% EtOAc:Hexane then 2 to 5% MeOH/EtOAc to provide 108 mg of the desired amide as a yellow solid.

1H NMR (500 MHz, CD3OD): 8.43 (s), 8.39 (s), 1H, 8.02~7.97 (m, 1H); 7.84~7.81 (m, 1H); 7.69~7.66 (m, 1H); 7.54~7.35 (m, 3H); 4.13~1.21 (m, 9H)

LC/MS: (ES+) m/z (m+H)+=475; RT=1.19, 1.27.

Example 11

N-(1-{2-[4-Fluoro-7-(1H-pyrazol-3-yl)-1H-indol-3-yl]-2-oxo-acetyl}-pyrrolidin-3-ylmethyl)-benzamide

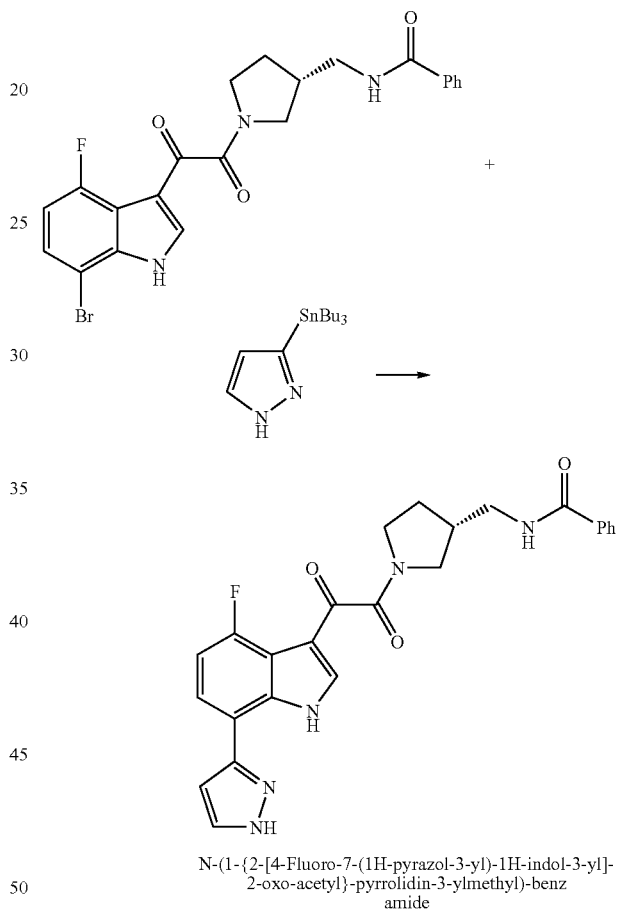

N-(1-{2-[4-Fluoro-7-(1H-pyrazol-3-yl)-1H-indol-3-yl]-2-oxo-acetyl}-pyrrolidin-3-ylmethyl)-benzamide The bromide (0.12 mmol, 59 mg), the pyrazole stannane (0.24 mmol, 86 mg), and palladium tetrakis triphenyl phosphine (0.012 mmol, 14 mg) were dissolved in 0.5 mL of dry dioxane and heated in a sealed tube at 140 to 145° C. for 17 h. After cooling to room temperature, the reaction was filtered through filter paper and the filtrate concentrated by rotary evaporation. The residue was dissolved in 2 mL of MeOH and purified using preparative thin layer chromatography to provide 12.6 mg of the desired pyrazole as a light yellow solid.

1H NMR (500 MHz, CD3OD): 8.62~8.57 (m, 1H), 8.32~8.30 (m, 1H); 7.92~7.15 (m, 10H); 4.05~1.82 (m, 9H)

LC/MS: (ES+) m/z (m+H)+=475; RT=1.01, 1.10.

Example 12

N-(1-{2-[4-Fluoro-7-(1H-pyrazol-3-yl)-1H-indol-3-yl]-2-oxo-acetyl}-pyrrolidin-3-ylmethyl)-benzamide

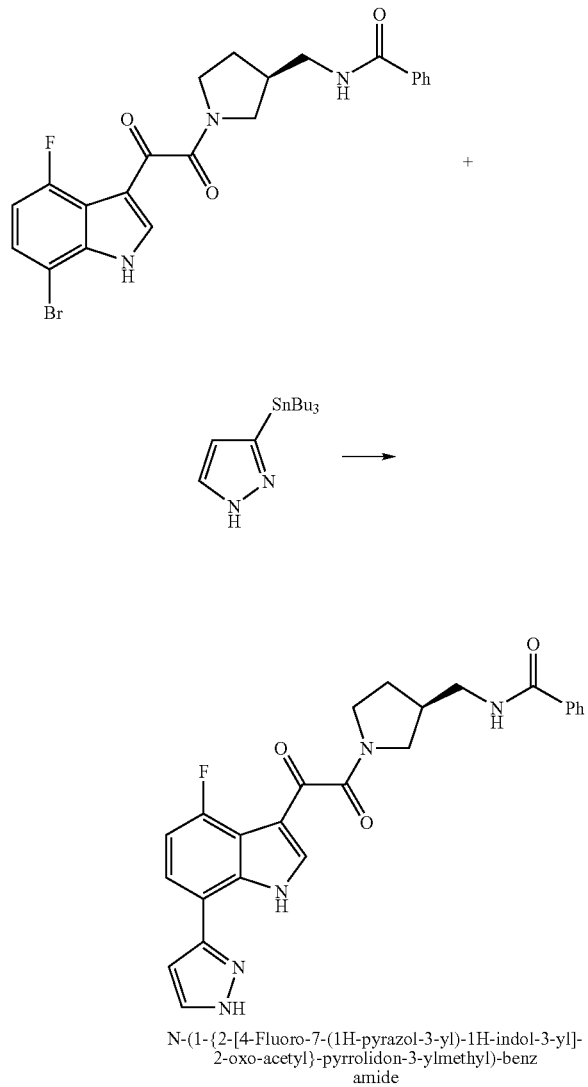

N-(1-{2-[4-Fluoro-7-(1H-pyrazol-3-yl)-1H-indol-3-yl]-2-oxo-acetyl}-pyrrolidon-3-ylmethyl)-benzamide The bromide (0.046 mmol, 22 mg), the pyrazole stannane (0.092 mmol, 33 mg), and palladium tetrakis triphenyl phosphine (10 mg) were dissolved in 0.5 mL of dry dioxane and heated in a sealed tube at 140 to 145° C. for 17 h. After cooling to room temperature, the reaction was filtered through filter paper and the filtrate concentrated by rotary evaporation. The residue was dissolved in 2 mL of MeOH and purified using preparative thin layer chromatography to provide 4.8 mg of the desired pyrazole as a light yellow solid.

1H NMR (500 MHz, CD3OD): 8.60~8.54 (m, 1H), 8.29~8.28 (m, 1H); 7.91~7.15 (m, 10H); 4.06~1.80 (m, 9H)

LC/MS: (ES+) m/z (m+H)+=475; RT=1.01, 1.10.

Example 13

2-(N-benzoylaminoethyl)-1-[(indol-3-yl)-2-oxoacetyl]-pyrrolidine

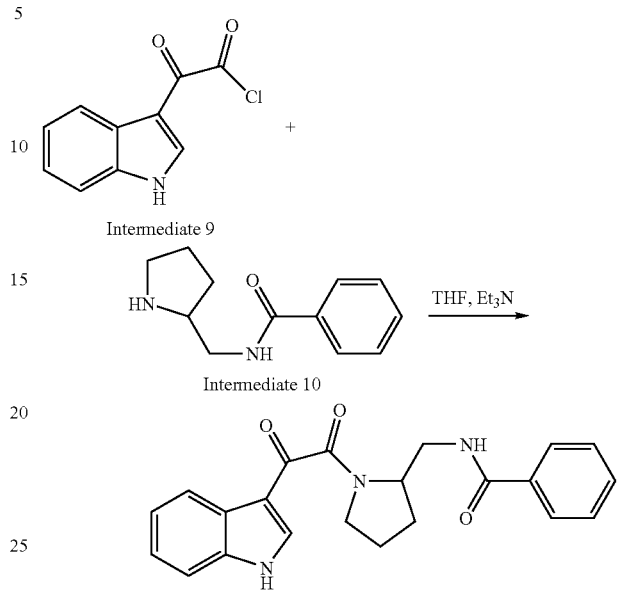

Preparation of Compound C, 2-(N-benzoylaminoethyl)-1-[(indol-3-yl)-2-oxoacetyl]-pyrrolidine Tri-ethylamine (1 ml) was added into a solution of indole-3-glyoxylyl chloride, intermediate 9 (50 mg, purchased from Lancaster) and intermediate 10 2-(N-benzoylaminoethyl)-pyrrolidine (49 mg, Wang, et al, *Tetrahedron Lett.* 1999, 40, 6745-6747) in THF (5 ml). After the reaction was stirred for 10 hours, the solvents were removed under vacuum to afford a residue which was purified using Shimadzu automated preparative HPLC System to give 2-(N-benzoylaminoethyl)-1-[(indol-3-yl)-2-oxoacetyl]-pyrrolidine (20 mg). Start %=0 Final %=100

Gradient time=2 minute

Flow Rate=5 ml/min

Wavelength=220

Column: XTERRA ms C18 4.6×30 mm

Rf=1.57 minute

MS (M+H) for C22H22N3O3

Cald=376.17

Obsd=376.23

Example 14

1H-Indole-3-carboxylic acid (1-benzoyl-pyrrolidin-3-yl)-methyl-amide

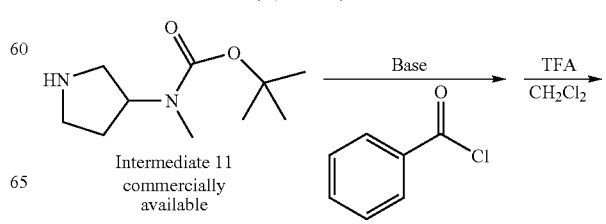

Intermediate 11 commercially available

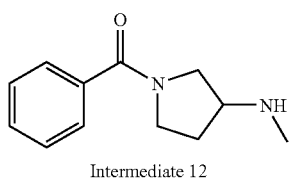

Intermediate 12

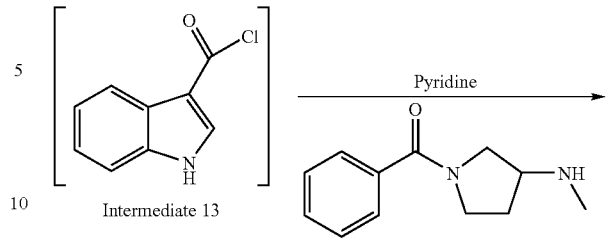

Intermediate 13 → Intermediate 12

The procedure is the same as the following one, which was described in Blair et. al. PCT WO 00/76521

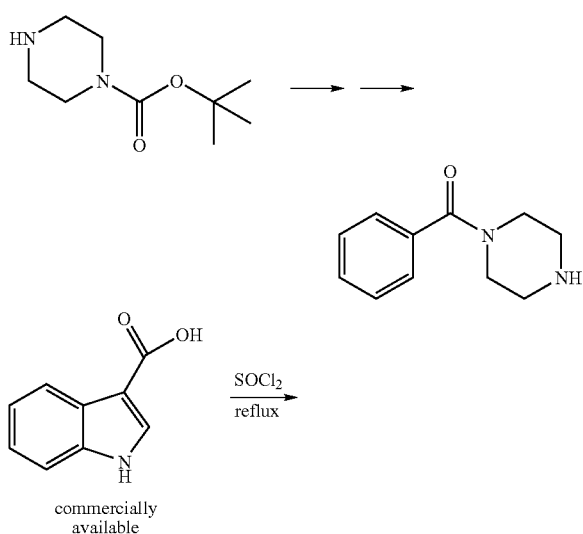

commercially available

Indole 3-carboxylic acid, (2.0 g) was dissolved in 5 ml of SOCl$_2$. The mixture was heated to reflux for 30 minutes. Removal of excess of SOCl$_2$ under vacuum provided intermediate 9, indole 3-carbonyl chloride, which was carried to the next step without further purification.

A mixture of indole 3-carbonyl chloride, intermediate 9 (50 mg), N-Benzoyl-3-methylamino-pyrrolidine, intermediate 10, (57 mg), pyridine (44 mg) in THF (5 ml) was stirred at room temperature for 10 hours. Solvents were removed under vacuum, and the residue was purified using a Shimadzu automated preparative HPLC System to give 78 mg of the compound of example 14, N-Benzoyl-3-[N-(indol-3-yl-carbonyl)-N-methyl]amino-pyrrolidine:

MS m/z: (M+H)$^+$ calcd for C$_{21}$H$_{19}$FN$_3$O$_3$: 348.17. found 348.22. HPLC retention time: 1.40p minutes (column A).

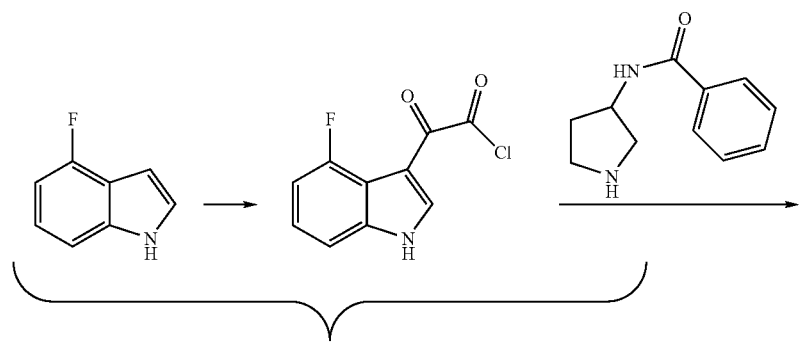

Procedure described in Blair et. al. PCT WO 00/76521

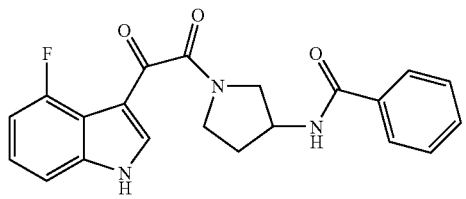

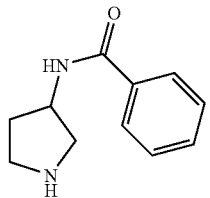

preparation described in Wang, T; Zhang, Z.; Meanwell, N. A. Selective Benzoylation of Primary Amines in the Presence of Secondary Amines *Tetrahedron Lett.* 1999, 40, 6745-6747.

Biology

"μM" means micromolar;
"mL" means milliliter;
"μl" means microliter;
"mg" means milligram;

The materials and experimental procedures used to obtain the results reported in Tables 1-2 are described below.

Cells:

Virus production-Human embryonic Kidney cell line, 293, propagated in Dulbecco's Modified Eagle Medium (Life Technologies, Gaithersburg, Md.) containing 10% fetal Bovine serum (FBS, Sigma, St. Louis, Mo.).

Virus infection-Human epithelial cell line, HeLa, expressing the HIV-1 receptors CD4 and CCR5 was propagated in Dulbecco's Modified Eagle Medium (Life Technologies, Gaithersburg, Md.) containing 10% fetal Bovine serum (FBS, Sigma, St. Louis, Mo.) and supplemented with 0.2 mg/mL Geneticin (Life Technologies, Gaithersburg, Md.) and 0.4 mg/mL Zeocin (Invitrogen, Carlsbad, Calif.).

Virus—Single-round infectious reporter virus was produced by co-transfecting human embryonic Kidney 293 cells with an HIV-1 envelope DNA expression vector and a proviral cDNA containing an envelope deletion mutation and the luciferase reporter gene inserted in place of HIV-1 nef sequences (Chen et al, Ref. 41). Transfections were performed using lipofectAMINE PLUS reagent as described by the manufacturer (Life Technologies, Gaithersburg, Md.).

Experiment

1. Compound was added to HeLa CD4 CCR5 cells plated in 96 well plates at a cell density of $1 \times 10^3$ cells per well in 100 μl Dulbecco's Modified Eagle Medium containing 10% fetal Bovine serum at a concentration of <20 μM.

2. 100 μl of single-round infectious reporter virus in Dulbecco's Modified Eagle Medium was then added to the plated cells and compound at an approximate multiplicity of infection (MOI) of 0.01, resulting in a final volume of 200 μl per well and a final compound concentration of <10 μM.

3. Samples were harvested 72 h after infection.

4. Viral infection was monitored by measuring luciferase expression from viral DNA in the infected cells using a luciferase reporter gene assay kit (Roche Molecular Biochemicals, Indianapolis, Ind.). Infected cell supernatants were removed and 50 μl of Dulbecco's Modified Eagle Medium (without phenol red) and 50 μl of luciferase assay reagent reconstituted as described by the manufacturer (Roche Molecular Biochemicals, Indianapolis, Ind.) was added per well. Luciferase activity was then quantified by measuring luminescence using a Wallac microbeta scintillation counter.

5. The percent inhibition for each compound was calculated by quantifying the level of luciferase expression in cells infected in the presence of each compound as a percentage of that observed for cells infected in the absence of compound and subtracting such a determined value from 100.

6. An $EC_{50}$ provides a method for comparing the antiviral potency of the compounds of this invention. The effective concentration for fifty percent inhibition ($EC_{50}$) was calculated with the Microsoft Excel Xlfit curve fitting software. For each compound, curves were generated from percent inhibition calculated at 10 different concentrations by using a four parameter logistic model (model 205). The $EC_{50}$ data for the compounds is shown in Tables 2-4. Table 1 is the key for the data in Table 2.

Results

TABLE 1

Biological Data Key for $EC_{50}$s

| Compounds* with $EC_{50}$s >5 μM | Compounds with $EC_{50}$s >1 μM but <5 μM | Compounds with EC50 >50 nM but not yet tested at higher concentrations | Compounds with EC50 <1 μM |
|---|---|---|---|
| Group C | Group B | Group A' | Group A |

*Some of these compounds may have been tested at a concentration lower than their $EC_{50}$ but showed some ability to cause inhibition and thus should be evaluated at a higher concentration to determine the exact $EC_{50}$.

In Tables 2-5, $X_2$, $X_4$ etc. indicates the point of attachment.
TABLE 2
Examples
| Table Entry (Example Number.) | Z | W | A | EC$_{50}$ Group from Table 1 |
|---|---|---|---|---|
| 1 (Example 1) | 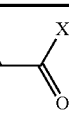 | 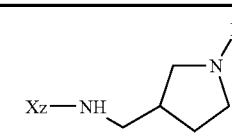 | 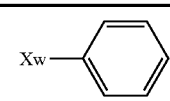 | A |
| 2 (Example 2) | 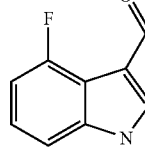 | 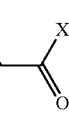 | 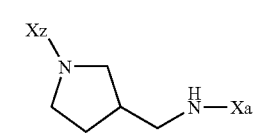 | C |
| 3 (Example 3) | 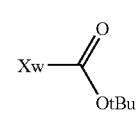 | 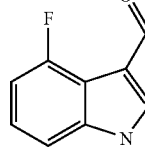 | 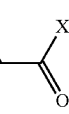 | A |
| 4 (Example 4) | 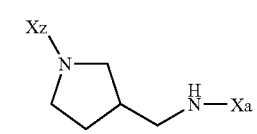 | 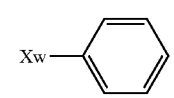 |  | A |
| 5 (Example 5) | 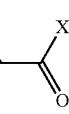 | 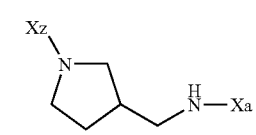 | 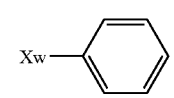 | B |
| 6 (Example 6) | 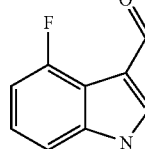 | 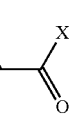 | 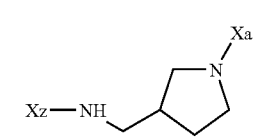 | C |

TABLE 2-continued

Examples

| Table Entry (Example Number.) | Z | W | A | EC$_{50}$ Group from Table 1 |
|---|---|---|---|---|
| 7 (Example 7) | 4-F, 7-COOH indole with Xz at 3-position via C(O)C(O)Xw | Xz—NH—CH$_2$—(pyrrolidin-3-yl), N—Xa | Xw—phenyl | B |
| 8 (Example 8) | 4-F, 7-CONHCH$_3$ indole with Xz at 3-position via C(O)C(O)Xw | Xz—NH—CH$_2$—(pyrrolidin-3-yl), N—Xa | Xw—phenyl | A |
| 9 (Example 9) | 4-F, 7-Br indole with Xz at 3-position via C(O)C(O)Xw | (S)-pyrrolidine, N—Xz, 3-CH$_2$NH—Xa | Xw—phenyl | A |
| 10 (Example 10) | 4-F, 7-Br indole with Xz at 3-position via C(O)C(O)Xw | (R)-pyrrolidine, N—Xz, 3-CH$_2$NH—Xa | Xw—phenyl | A |
| 11 (Example 11) | 4-F, 7-(1H-pyrazol-3-yl) indole with Xz at 3-position via C(O)C(O)Xw | (R)-pyrrolidine, N—Xz, 3-CH$_2$NH—Xa | Xw—phenyl | A |

TABLE 2-continued

Examples

| Table Entry (Example Number.) | Z | W | A | EC$_{50}$ Group from Table 1 |
|---|---|---|---|---|
| 12 (Example 12) | 4-fluoro-7-(1H-pyrazol-3-yl)indol-3-yl-glyoxylyl (Xw at carbonyl) | 3-(aminomethyl)pyrrolidinyl (Xz on N, Xa on NH) | Xw—phenyl | A |
| 13 (Example 13) | indol-3-yl-glyoxylyl (Xw) | 2-(aminomethyl)pyrrolidinyl (Xz on N, Xa on NH) | Xw—phenyl | A |
| 14 (Example 14) | indol-3-yl-carbonyl (Xw) | 3-(N-methylamino)-1-pyrrolidinyl (Xz—N(CH$_3$), Xa on ring N) | Xw—phenyl | C |
| 15 (Example 15) | indol-3-yl-glyoxylyl (Xw) | 3-aminopyrrolidinyl (Xz on N, Xa on NH) | Xw—phenyl | C |
| 16 (Example 16) | 4,6-difluoroindol-3-yl-glyoxylyl (Xw) | 3-(pyrrolidinylmethyl)amine (Xz—NH, Xa on ring N) | Xw—phenyl | A' |

The compounds of the present invention may be administered orally, parenterally (including subcutaneous injections, intravenous, intramuscular, intrasternal injection or infusion techniques), by inhalation spray, or rectally, in dosage unit formulations containing conventional non-toxic pharmaceutically acceptable carriers, adjuvants and diluents.

Thus, in accordance with the present invention, there is further provided a method of treating and a pharmaceutical composition for treating viral infections such as HIV infection and AIDS. The treatment involves administering to a patient in need of such treatment a pharmaceutical composition comprising a pharmaceutical carrier and a therapeutically effective amount of a compound of the present invention.

The pharmaceutical composition may be in the form of orally administrable suspensions or tablets; nasal sprays, sterile injectable preparations, for example, as sterile injectable aqueous or oleagenous suspensions or suppositories.

When administered orally as a suspension, these compositions are prepared according to techniques well known in the art of pharmaceutical formulation and may contain microcrystalline cellulose for imparting bulk, alginic acid or sodium alginate as a suspending agent, methylcellulose as a viscosity enhancer, and sweetners/flavoring agents known in the art. As immediate release tablets, these compositions may contain microcrystalline cellulose, dicalcium phosphate, starch, magnesium stearate and lactose and/or other excipients, binders, extenders, disintegrants, diluents, and lubricants known in the art.

The injectable solutions or suspensions may be formulated according to known art, using suitable non-toxic, parenterally acceptable diluents or solvents, such as mannitol, 1,3-butanediol, water, Ringer's solution or isotonic sodium chloride solution, or suitable dispersing or wetting and suspending agents, such as sterile, bland, fixed oils, including synthetic mono- or diglycerides, and fatty acids, including oleic acid.

The compounds of this invention can be administered orally to humans in a dosage range of 1 to 100 mg/kg body weight in divided doses. One preferred dosage range is 1 to 10 mg/kg body weight orally in divided doses. Another preferred dosage range is 1 to 20 mg/kg body weight in divided doses. It will be understood, however, that the specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

What is claimed is:

1. A compound, including pharmaceutically acceptable salts thereof, which is selected from the group consisting of

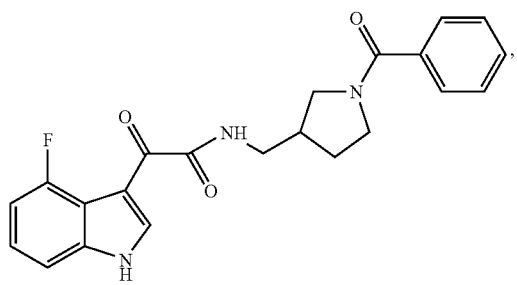

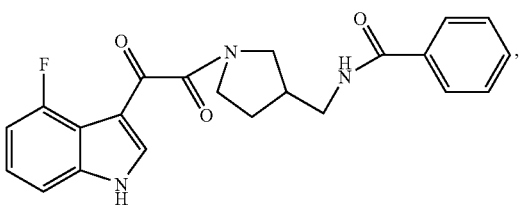

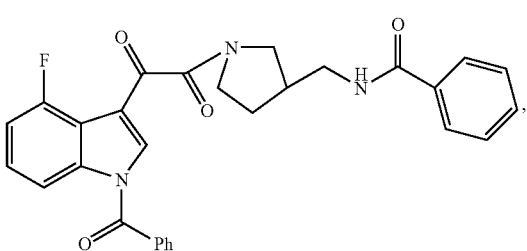

-continued

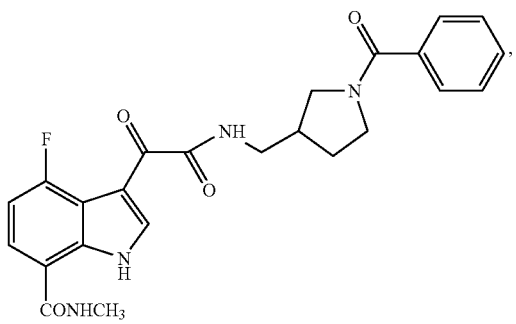

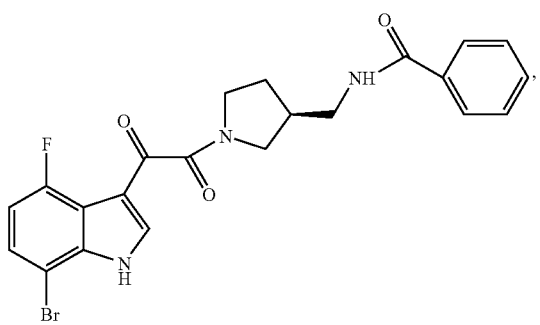

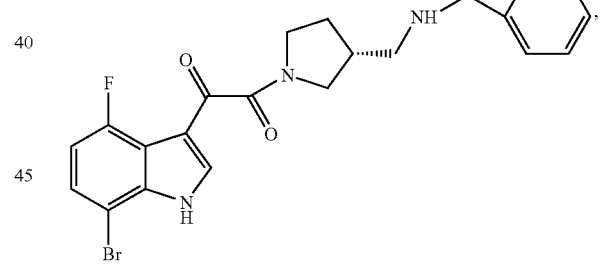

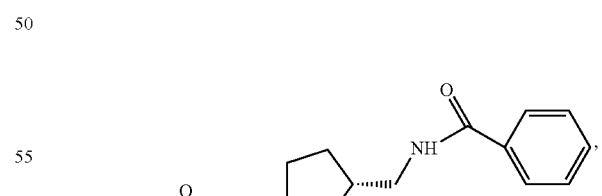

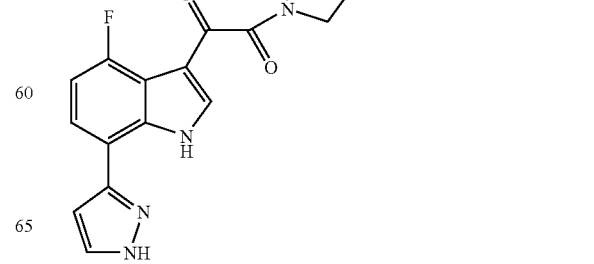

-continued
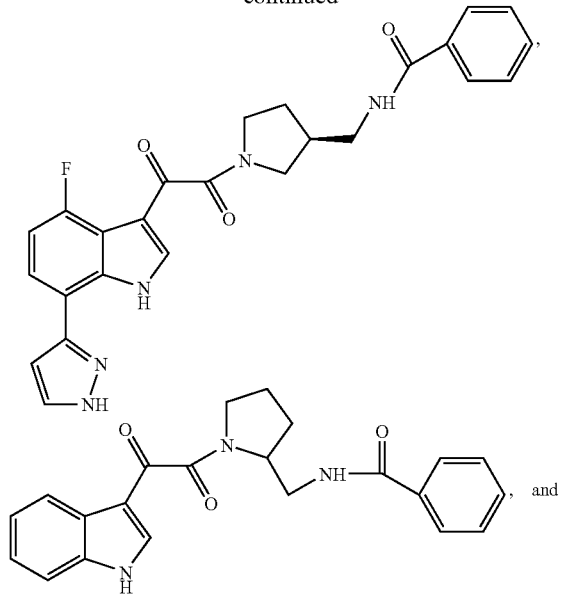
2. A pharmaceutical composition which comprises an antiviral effective amount of a compound, including pharmaceutically acceptable salts thereof, as claimed in claim 1, and one or more pharmaceutically acceptable carriers, excipients or diluents.
* * * * *